United States Patent
Liddicoat et al.

(10) Patent No.: US 8,617,189 B2
(45) Date of Patent: Dec. 31, 2013

(54) APPARATUS AND METHOD FOR MANIPULATING TISSUE

(76) Inventors: John R. Liddicoat, Boston, MA (US); William E. Cohn, Chestnut Hill, MA (US)

(*) Notice: Subject to any disclaimer, the term of this patent is extended or adjusted under 35 U.S.C. 154(b) by 0 days.

(21) Appl. No.: 12/932,218

(22) Filed: Feb. 18, 2011

(65) Prior Publication Data
US 2012/0010639 A1    Jan. 12, 2012

Related U.S. Application Data

(63) Continuation of application No. 10/724,854, filed on Dec. 1, 2003, now Pat. No. 7,892,245.

(60) Provisional application No. 60/429,568, filed on Nov. 29, 2002, provisional application No. 60/453,294, filed on Mar. 11, 2003, provisional application No. 60/458,128, filed on Mar. 27, 2003.

(51) Int. Cl.
*A61B 17/08*      (2006.01)

(52) U.S. Cl.
USPC ............................ 606/153; 606/151; 606/139

(58) Field of Classification Search
USPC ................. 606/151, 152, 153, 141, 142, 143; 607/133; 604/891.1; 128/898
See application file for complete search history.

(56) References Cited

U.S. PATENT DOCUMENTS

| | | | |
|---|---|---|---|
| 5,196,003 A | 3/1993 | Bilweis | |
| 5,345,949 A | 9/1994 | Shlain | |
| 5,865,827 A | 2/1999 | Bullister | |
| 6,197,022 B1 | 3/2001 | Baker | |
| 6,231,585 B1 | 5/2001 | Takahashi et al. | |
| 6,254,642 B1 | 7/2001 | Taylor | |
| 6,478,791 B1 | 11/2002 | Carter et al. | |
| 6,514,250 B1 | 2/2003 | Jahns et al. | |
| 6,544,271 B1 | 4/2003 | Adams et al. | |
| 6,551,328 B2 | 4/2003 | Kortenbach | |
| 6,558,400 B2 | 5/2003 | Deem et al. | |
| 6,592,596 B1 | 7/2003 | Geitz | |
| 6,663,639 B1 | 12/2003 | Laufer et al. | |
| 6,740,082 B2 * | 5/2004 | Shadduck | 606/41 |
| 6,835,200 B2 * | 12/2004 | Laufer et al. | 606/153 |
| 7,288,099 B2 | 10/2007 | Deem et al. | |
| 2001/0056282 A1 | 12/2001 | Sonnenschein et al. | |
| 2002/0082621 A1 | 6/2002 | Schurr et al. | |
| 2002/0156470 A1 | 10/2002 | Shadduck | |
| 2002/0193851 A1 | 12/2002 | Silverman et al. | |
| 2003/0065359 A1 | 4/2003 | Weller et al. | |

(Continued)

FOREIGN PATENT DOCUMENTS

| | | |
|---|---|---|
| WO | WO 97/03616 | 2/1997 |
| WO | WO 99/22649 | 5/1999 |

*Primary Examiner* — Vy Q Bui
(74) *Attorney, Agent, or Firm* — Pandiscio & Pandiscio

(57) ABSTRACT

Apparatus for reconfiguring tissue, the apparatus comprising a shaft having a distal end and a proximal end; at least one effector mechanism movably mounted to the distal end of the shaft, each effector mechanism comprising at least one gripping element for gripping tissue to that effector mechanism, the at least one effector mechanism being configured to capture the gripped tissue against said shaft, at least one actuating mechanism mounted to the proximal end of the shaft, and at least one connection mechanism connecting the at least one actuating mechanism to the at least one effector mechanism, whereby a user may utilize the at least one actuating mechanism to actuate the at least one effector mechanism so as to reconfigure tissue.

34 Claims, 24 Drawing Sheets

(56) References Cited

U.S. PATENT DOCUMENTS

| | | |
|---|---|---|
| 2003/0120289 A1 | 6/2003 | McGuckin et al. |
| 2003/0171664 A1 | 9/2003 | Wendlandt |
| 2003/0171760 A1 | 9/2003 | Gambale |
| 2003/0176883 A1 | 9/2003 | Sauer et al. |

* cited by examiner

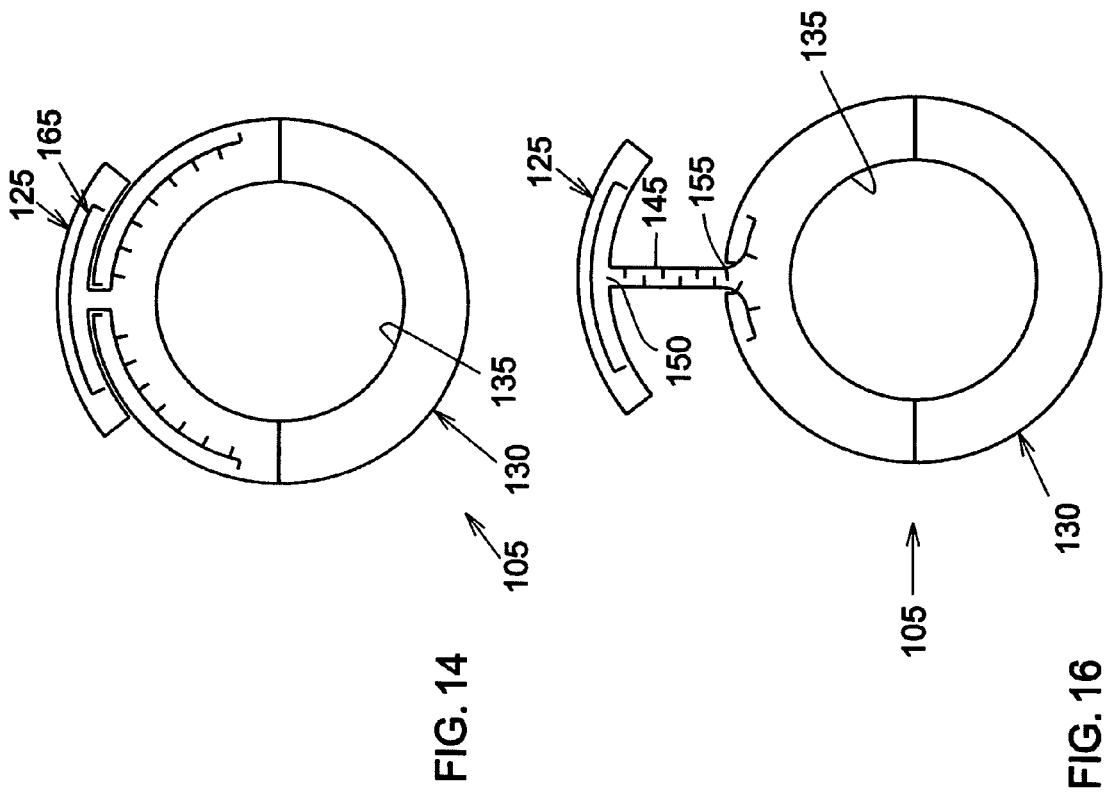

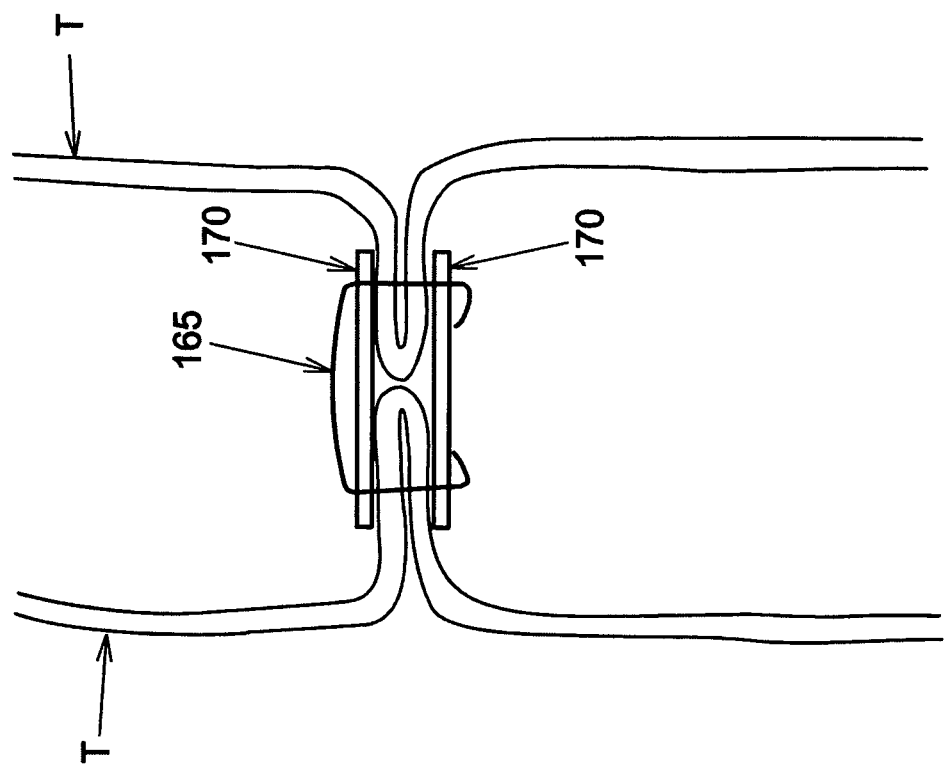

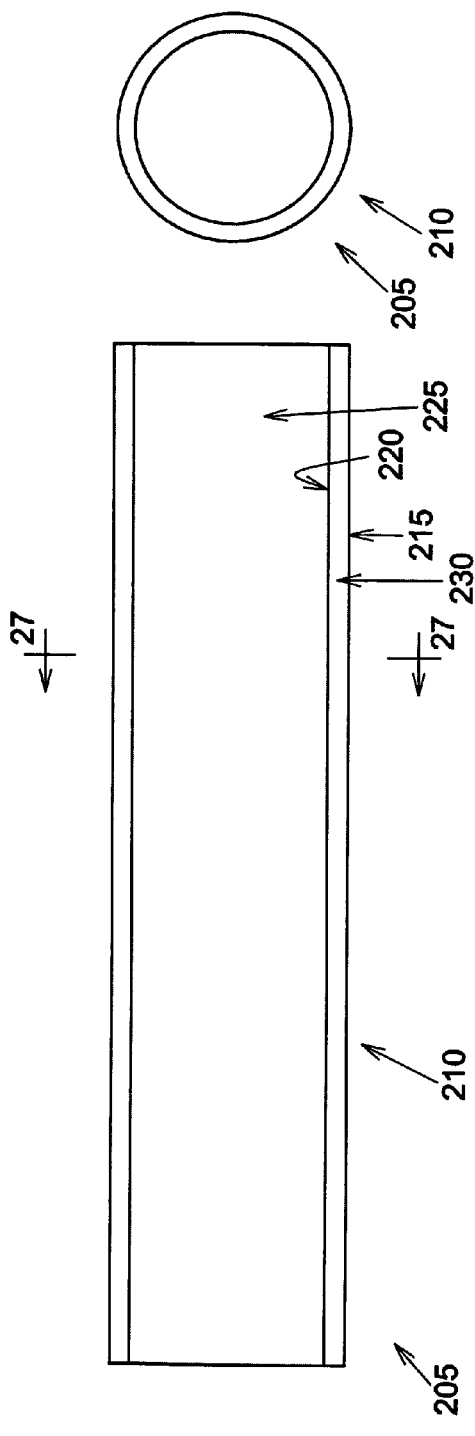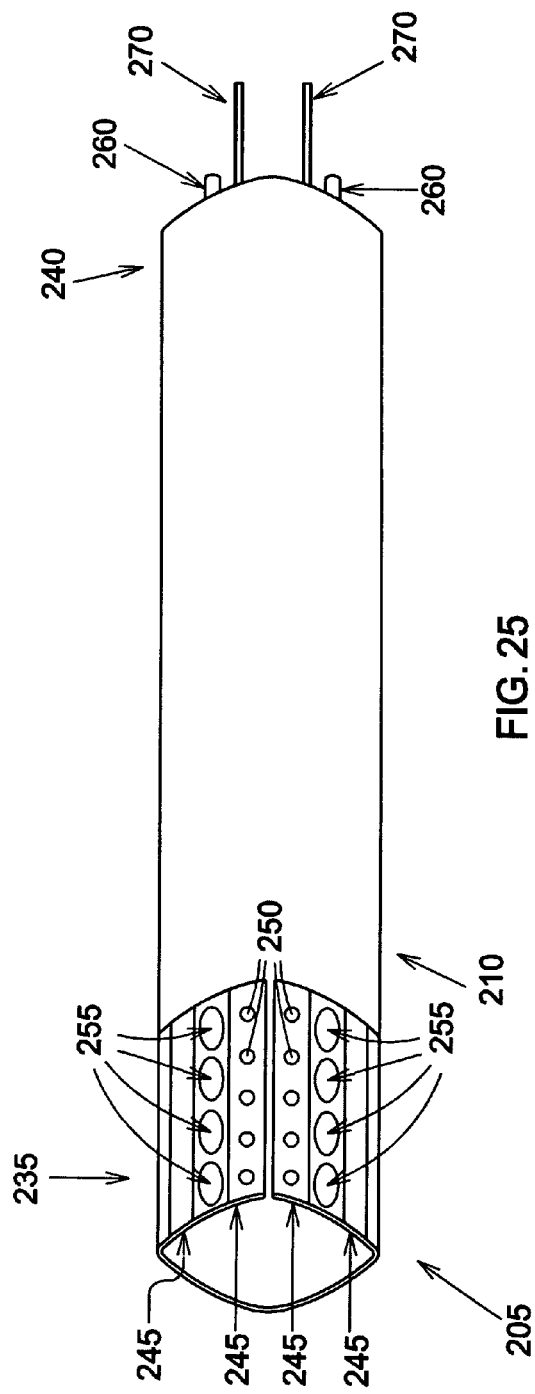

APPARATUS AND METHOD FOR MANIPULATING TISSUE

REFERENCE TO PENDING PRIOR PATENT APPLICATIONS

This patent application is a continuation of pending prior U.S. patent application Ser. No. 10/724,854, filed Dec. 1, 2003 now U.S. Pat. No. 7,892,245 by John R. Liddicoat et al. for APPARATUS AND METHOD FOR MANIPULATING TISSUE, which in turn claims benefit of:

(1) prior U.S. Provisional Patent Application Ser. No. 60/429,568, filed Nov. 29, 2002 by John Randall Liddicoat et al. for TISSUE MANIPULATING METHODS AND DEVICES;

(2) prior U.S. Provisional Patent Application Ser. No. 60/453,294, filed Mar. 11, 2003 by John Randall Liddicoat et al. for TISSUE MANIPULATING METHODS AND DEVICES; and (3) prior U.S. Provisional Patent Application Ser. No. 60/458,128, filed Mar. 27, 2003 by John Randall Liddicoat et al. for TISSUE MANIPULATING METHODS AND DEVICES.

The above-identified patent applications are hereby incorporated herein by reference.

FIELD OF THE INVENTION

This invention relates to medical apparatus and methods in general, and more particularly to medical apparatus and methods for manipulating tissue.

BACKGROUND OF THE INVENTION

Gastroesophageal reflux disease (GERD) is the most common gastrointestinal problem in humans. GERD occurs when the esophageal exposure to acid from the stomach is greater than that of the normal population. GERD may be a result from a defect in the stomach, the esophageal sphincter, or the esophagus. Heartburn is the most common symptom. GERD can result in complications such as esophagitis, esophageal ulceration, esophageal stricture, esophageal metaplasia (i.e., Barrett's esophagus) and short esophagus syndrome. Currently, patients with GERD are treated with both medicine and/or surgery. The goal of the treatment options is to decrease the esophageal exposure to the stomach acid.

One possible way to treat GERD may be to alter the configuration of the esophagus and/or stomach. Thus, it would be beneficial to provide a novel apparatus and method for manipulating the esophagus and/or stomach so as to alter the configuration of the esophagus and/or stomach and thereby treat GERD.

Severe obesity is associated with a large number of health-related problems. Several of these problems are underlying causes of earlier mortality for obesity. Obesity may be treated with mechanical interventions including surgical procedures.

One possible way to treat obesity may be to manipulate the tissues of the gastrointestinal tract to alter the size and/or shape of the stomach. Thus, it would be advantageous to provide a novel apparatus and method for manipulating the tissues of the gastrointestinal tract so as to alter the size and/or shape of the stomach and thereby treat obesity.

Still other medical disorders may be treated by manipulating tissue in selected ways, e.g., such as by bringing opposite walls of a tube of tissue into proximity with one another, or for creating a cylinder or tube of tissue wrapped partially or entirely by an outer layer of tissue, etc. Thus, it would be advantageous to provide a novel apparatus and method for manipulating tissue so as to achieve a desired shape.

SUMMARY OF THE INVENTION

The present invention provides a novel apparatus and method for manipulating tissue so as to provide a therapeutic benefit.

In one form of the invention, there is provided an apparatus for reconfiguring tissue, said apparatus comprising:

a shaft having a distal end and a proximal end;

at least one effector mechanism movably mounted to said distal end of said shaft, each said effector mechanism comprising at least one gripping element for gripping tissue to that effector mechanism, said at least one effector mechanism being configured to capture the gripped tissue against said shaft;

at least one actuating mechanism mounted to said proximal end of said shaft; and at least one connection mechanism connecting said at least one actuating mechanism to said at least one effector mechanism, whereby a user may utilize said at least one actuating mechanism to actuate said at least one effector mechanism so as to reconfigure tissue.

In another form of the invention, there is provided an apparatus for reconfiguring tissue, said apparatus comprising:

a shaft having a distal end and a proximal end, wherein said distal end of said shaft comprises at least one gripping element for drawing tissue against said shaft and for selectively maintaining the tissue in such engagement;

two effector mechanisms movably mounted to said distal end of said shaft, each said effector mechanism comprising at least one gripping element for gripping tissue to that effector mechanism, said two effector mechanisms being configured to capture the gripped tissue against said shaft, wherein said distal end of said shaft comprises a longitudinal axis, wherein said two effector mechanisms are pivotally mounted to said shaft along a pivot axis extending parallel to said longitudinal axis of said distal end of said shaft, wherein said two effector mechanisms are configured to move between (i) a closed position wherein said two effector mechanisms fold concentrically about said distal end of said shaft, and (ii) an open position wherein said two effector mechanisms rise like wings over said shaft, and wherein said at least one gripping element comprises a suction pod for drawing tissue against the effector mechanism and for maintaining the tissue in such engagement while suction is maintained;

at least one actuating mechanism mounted to said proximal end of said shaft; and at least one connection mechanism connecting said at least one actuating mechanism to said two effector mechanisms, whereby a user may utilize said at least one actuating mechanism to actuate said two effector mechanisms so as to reconfigure tissue.

In another form of the invention, there is provided an apparatus for reconfiguring tissue, said apparatus comprising:

a shaft having a distal end and a proximal end, wherein said distal end of said shaft comprises at least one gripping element for drawing tissue against said shaft and for maintaining the tissue in such engagement while suction is maintained;

an effector mechanism movably mounted to said distal end of said shaft, said effector mechanism comprising at least one gripping element for gripping tissue to that effector mechanism, said effector mechanism being configured to capture the gripped tissue against said shaft, wherein said distal end of said shaft comprises a longitudinal axis, wherein said effector mechanism is pivotally mounted to said shaft along a pivot axis extending transverse to said longitudinal axis of said distal end of said shaft, wherein said effector mechanism is configured to move between (i) a closed position wherein said effector mechanism folds concentrically about said distal end of said shaft, and (ii) an open position wherein said effector mechanism rises over said shaft, and wherein said at least one griping element comprises a suction pod for drawing tissue against the effector mechanism and for maintaining tissue in such engagement while suction is maintained;

at least one actuating mechanism mounted to said proximal end of said shaft; and at least one connection mechanism connecting said at least one actuating mechanism to said effector mechanism, whereby a user may utilize said at least one actuating mechanism to actuate said effector mechanism so as to reconfigure tissue.

In another form of the invention, there is provided an apparatus for reconfiguring tissue, said apparatus comprising:

a shaft having a distal end and a proximal end;

a plurality of effector mechanisms mounted to said distal end of said shaft, each said effector mechanism comprising at least one gripping element for gripping tissue to that effector mechanism, said plurality of effector mechanisms being configured to capture the gripped tissue against said shaft, wherein said distal end of said shaft comprises a longitudinal axis, wherein said plurality of effector mechanisms extend parallel to said longitudinal axis of said distal end of said shaft, wherein said plurality of effector mechanisms are configured to move between (i) a first position wherein said plurality of effector mechanisms collectively form a tubular configuration, and (ii) a second position wherein said plurality of effector mechanisms collectively form a non-tubular configuration, and wherein said at least one gripping element comprises a suction pod for drawing tissue against the effector mechanism and for maintaining the tissue in such engagement while suction is maintained;

at least one actuating mechanism mounted to said proximal end of said shaft; and at least one connection mechanism connecting said at least one actuating mechanism to said plurality of effector mechanisms, whereby a user may utilize said at least one actuating mechanism to actuate said plurality of effector mechanisms so as to reconfigure tissue.

In another form of the invention, there is provided a method for reconfiguring tissue, said method comprising:

providing apparatus comprising:

a shaft having a distal end and a proximal end, wherein said distal end of said shaft comprises at least one gripping element for drawing tissue against said shaft and for selectively maintaining the tissue in such engagement;

two effector mechanisms movably mounted to said distal end of said shaft, each said effector mechanism comprising at least one gripping element for gripping tissue to that effector mechanism, said two effector mechanisms being configured to capture the gripped tissue against said shaft, wherein said distal end of said shaft comprises a longitudinal axis, wherein said two effector mechanisms are pivotally mounted to said shaft along a pivot axis extending parallel to said longitudinal axis of said distal end of said shaft, wherein said two effector mechanisms are configured to move between (i) a closed position wherein said two effector mechanisms fold concentrically about said distal end of said shaft, and (ii) an open position wherein said two effector mechanisms rise like wings over said shaft, and wherein said at least one gripping element comprises a suction pod for drawing tissue against the effector mechanism and for maintaining the tissue in such engagement while suction is maintained;

at least one actuating mechanism mounted to said proximal end of said shaft; and at least one connection mechanism connecting said at least one actuating mechanism to said two effector mechanisms, whereby a user may utilize said at least one actuating mechanism to actuate said two effector mechanisms so as to reconfigure tissue;

positioning said two effector mechanisms in said closed position;

advancing said apparatus so that said distal end of said shaft is positioned adjacent tissue to be reconfigured;

positioning said two effector mechanisms in said open position;

gripping tissue against said distal end of said shaft and against said two effector mechanisms; and positioning said two effector mechanisms in said closed position so as to reconfigure the gripped tissue and capture that tissue against said shaft.

In another form of the invention, there is provided a method for reconfiguring tissue, said method comprising:

providing apparatus comprising:

a shaft having a distal end and a proximal end, wherein said distal end of said shaft comprises at least one gripping element for drawing tissue against said shaft and for maintaining the tissue in such engagement while suction is maintained;

an effector mechanism movably mounted to said distal end of said shaft, said effector mechanism comprising at least one gripping element for gripping tissue to that effector mechanism, said effector mechanism being configured to capture the gripped tissue against said shaft, wherein said distal end of said shaft comprises a longitudinal axis, wherein said effector mechanism is pivotally mounted to said shaft along a pivot axis extending transverse to said longitudinal axis of said distal end of said shaft, wherein said effector mechanism is configured to move between (i) a closed position wherein said effector mechanism folds concentrically about said distal end of said shaft, and (ii) an open position wherein said effector mechanism rises over said shaft, and wherein said at least one griping element comprises a suction pod for drawing tissue against the effector mechanism and for maintaining tissue in such engagement while suction is maintained;

at least one actuating mechanism mounted to said proximal end of said shaft; and at least one connection mechanism connecting said at least one actuating mechanism to said effector mechanism, whereby a user may utilize said at least one actuating mechanism to actuate said effector mechanism so as to reconfigure tissue;

positioning said effector mechanism in said closed position;

advancing said apparatus so that said distal end of said shaft is positioned adjacent tissue to be reconfigured;

positioning said effector mechanism in said open position;

gripping tissue against said distal end of said shaft and against said effector mechanism; and positioning said effector mechanism in said closed position so as to reconfigure the gripped tissue and capture that tissue against said shaft.

In another form of the invention, there is provided a method for reconfiguring tissue, said method comprising:
providing apparatus comprising:
a shaft having a distal end and a proximal end;
a plurality of effector mechanisms mounted to said distal end of said shaft, each said effector mechanism comprising at least one gripping element for gripping tissue to that effector mechanism, said plurality of effector mechanisms being configured to capture the gripped tissue against said shaft, wherein said distal end of said shaft comprises a longitudinal axis, wherein said plurality of effector mechanisms extend parallel to said longitudinal axis of said distal end of said shaft, wherein said plurality of effector mechanisms are configured to move between (i) a first position wherein said plurality of effector mechanisms collectively form a tubular configuration, and (ii) a second position wherein said plurality of effector mechanisms collectively form a non-tubular configuration, and wherein said at least one gripping element comprises a suction pod for drawing tissue against the effector mechanism and for maintaining the tissue in such engagement while suction is maintained;
at least one actuating mechanism mounted to said proximal end of said shaft; and
at least one connection mechanism connecting said at least one actuating mechanism to said plurality of effector mechanisms, whereby a user may utilize said at least one actuating mechanism to actuate said plurality of effector mechanisms so as to reconfigure tissue;
positioning said effector mechanisms in said first position;
advancing said apparatus so that said distal end of said shaft is positioned adjacent tissue to be reconfigured;
gripping tissue against said distal end of said shaft and against said effector mechanisms; and
positioning said effector mechanisms in said second position so as to reconfigure the gripped tissue and capture that tissue against said shaft.

In another form of the invention, there is provided a method for treating GERD, comprising:
creating a neoesophagus that extends into the abdomen.

BRIEF DESCRIPTION OF THE DRAWINGS

These and other objects and features of the present inventions will be more fully disclosed or rendered obvious by the following detailed description of the preferred embodiments of the invention, which is to be considered together with the accompanying drawings wherein like numbers refer to like parts and further wherein:

FIGS. 13-18 are a series of schematic views showing a second preferred embodiment of the present invention;

FIGS. 23 and 24 are schematic views showing alternative forms of the procedure shown in FIGS. 19-22; and FIGS. 25-31 are a series of schematic views showing a third preferred form of the present invention.

DETAILED DESCRIPTION OF THE PREFERRED EMBODIMENT

General Description

Figure 1:
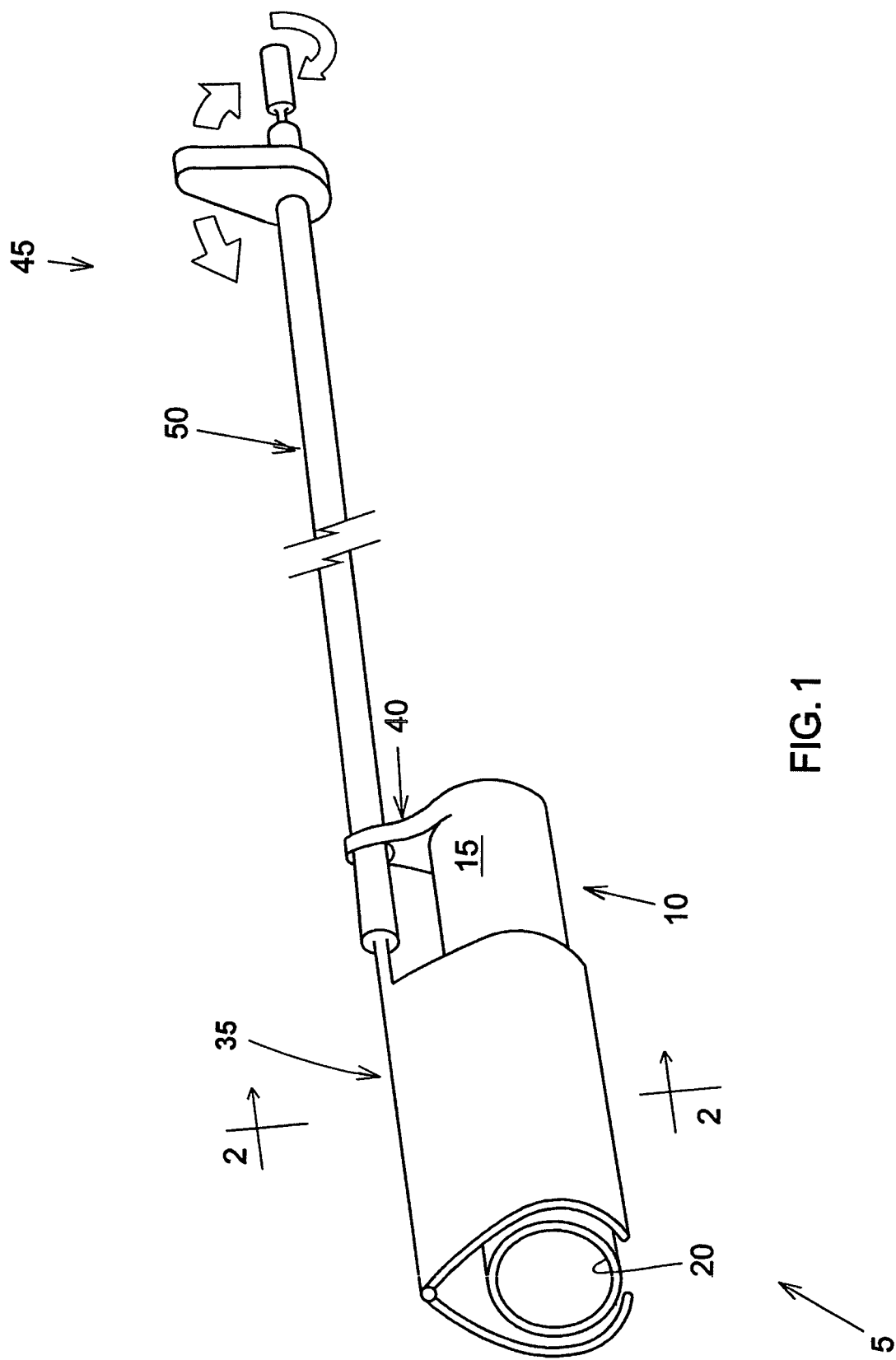
FIGS. 1-4 are a series of schematic views showing a first preferred embodiment of the present invention.
Figure 2:
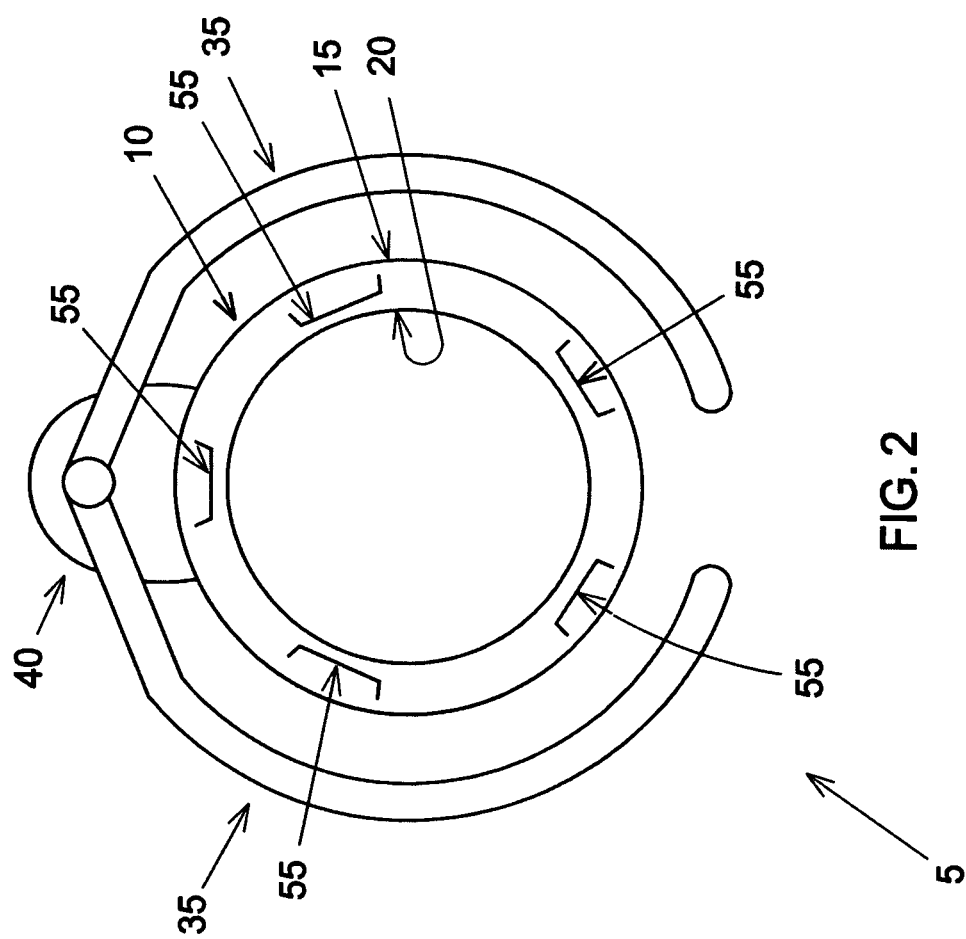
Figure 3:
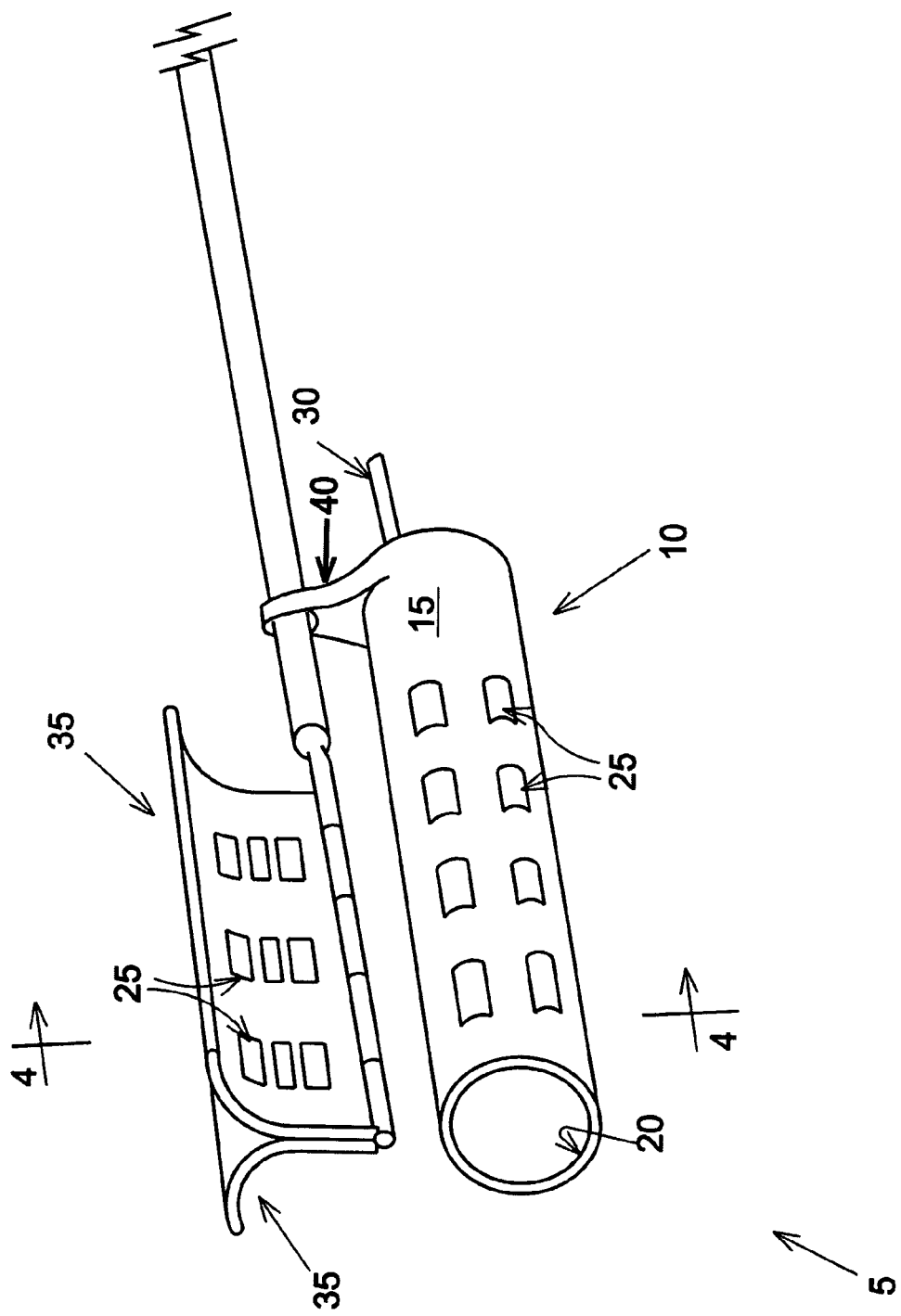
Figure 4:
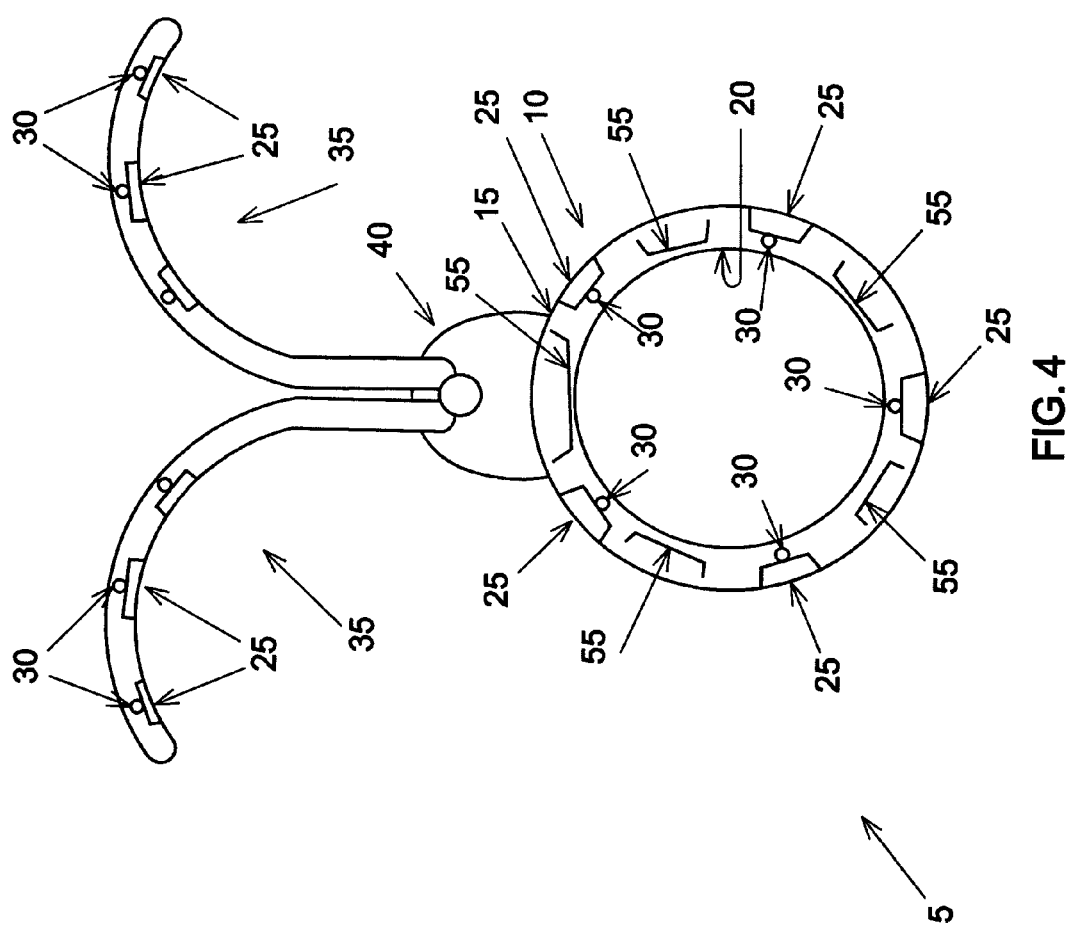

The present invention relates to apparatus and methods for manipulating tissue. This invention can be used to manipulate tissue so as to create many different shapes and configurations. For example, in one form of the invention, apparatus is provided which can be used to bring opposite walls of a hollow organ or viscus into close apposition such that they form a tube of tissue, and/or apparatus is provided which can be used to create a cylinder or tube of tissue wrapped partially or entirely by an out-pouching of the same hollow viscus. More particularly, in one form of the present invention, apparatus is provided that can be used to create an inner tube of stomach or esophagus wrapped by a pouch of stomach, and/or apparatus is provided which can be used to create a tube of stomach in continuity with the esophagus, whereby to essentially create a neoesophagus which may be wrapped partially or entirely by an outer pouch of the stomach, the lumen of which is in continuity with the main lumen of the stomach, esophagus, and neoesophagus.

The present invention comprises multiple components which may be used alone, together, or in various combinations. The present invention may provide stabilizing means (such as suction, pins, barbs, hooks, adhesive, glue, magnets, etc.) to effect conformational changes in tissue configurations, and fixation means (such as staples, pins, barbs, hooks, adhesive, glue, magnets, etc.) to secure the tissue in such configuration after the stabilizing means are withdrawn.

In one aspect of the invention, novel apparatus may be used to treat disease states. One of these disease states is GERD. Another of these disease states is obesity. Hereinafter, various embodiments of the invention will sometimes be discussed in the context of these two disease states, i.e., GERD and obesity. However, it is to be appreciated that this is intended to be by way of example and not limitation, and that the present invention may be applied to the treatment of other disease states as well.

In one preferred embodiment of the present invention, the apparatus comprises a flexible tube with effector mechanisms on the distal end and actuating mechanisms on the proximal end. If desired, other devices (including but not limited to endoscopes, cables, pulleys, staplers, magnets, other tubes, devices for conveying a variety of energy sources, tubes for delivering adhesives and glues, etc.) may be passed through the lumen of the flexible tube. In addition to the foregoing, the walls of the tube may also have one or more additional lumens through which one or more devices may be passed.

The effector mechanisms may be used to grasp tissue to assist in manipulating that tissue. The effector mechanisms may take any form that will grip the tissue, such as suction, one or more hooks, one or more staples, glue, magnets, etc. For purposes of illustration but not limitation, the preferred embodiments disclosed herein utilize suction to grasp the tissue.

In one preferred form of effector mechanism, the suction is applied to the tissue through pods. These pods are mounted on the distal end of the flexible tube. The pods may comprise any shape or configuration consistent with the application intended. By way of example but not limitation, in the preferred embodiments disclosed herein, the pods comprise a low-profile curvilinear box with one or more holes formed therein. The side of the box with the one or more holes contacts the tissue. Another side of the box has one or more ports to which suction is applied. Suction can be applied to the port through one or more small conduits which run inside, outside, or in the sidewall of the flexible tube. Suction can be applied to the conduits by any means capable of generating satisfactory suction (e.g., a suction pump). By way of example but not limitation, in the preferred embodiments disclosed herein, the suction conduits run inside the sidewall of the flexible tube. The distal ends of the conduits are connected to the pods, and the proximal ends of the conduits are connected to the suction source.

The actuating mechanisms are disposed at least in part on the proximal end of the flexible tube. The actuating mechanisms are used to effect movement of the effector mechanisms which engage and manipulate the tissue. The actuating mechanisms may move the effector mechanisms by any of the various means well known in the art including, but not limited to, cables, cogs, motor systems, remote wireless systems, etc. By way of example but not limitation, in the preferred embodiments disclosed herein, cables are used to move the effector mechanisms. More particularly, the effector mechanisms are connected to a series of cables that run within the flexible tube. These cables run the length of the tube, from the distal end to the proximal end. This allows a doctor to manipulate the effector mechanisms at distal end of the device by turning or pulling and releasing the cables on the proximal end of the device.

The flexible tube itself can be directly maneuvered by the doctor, or the flexible tube can be mounted on another instrument (e.g., an endoscope) and passively steered by maneuvering of that other instrument.

In one preferred form of the invention, the apparatus may comprise a visualization unit to assist in appropriately directing the apparatus. This visualization unit may be an integral component of the system, similar to a flexible endoscope or ultrasound probe or wireless video transmitter, etc. Alternatively, the visualization unit may be independent of the system, e.g., it may comprise a CT or MRI machine. Alternatively, the present invention could be employed without visual aid. By way of example but not limitation, in the preferred embodiments disclosed herein, an endoscope is used to assist in visualization, with the endoscope passing through the central lumen of the flexible tube.

Once the effector mechanisms have manipulated the tissue into proper position, the tissue can be held in position by various types of fixation mechanisms including, but not limited to, staples, sutures, magnets, glue, etc. By way of example but not limitation, in several of the preferred embodiments disclosed herein, staples are located in the flexible tube, and the effector mechanisms can act as anvils for the staples. These staples may be actuated by actuating mechanisms (e.g., cables) similar to those used to manipulate the effector mechanisms.

Furthermore, once the tube or fold of tissue has been formed and secured by one of the fixation mechanisms, it may be desirable to fold additional tissue around the tube. This additional tissue can be held around the underlying tube or fold of tissue by various mechanisms including, but not limited to, staples, magnets, sutures, glue, etc.

As noted above, in some cases it may be desirable to create tubes or folds of tissue of varying sizes and shapes. One way to do this is by providing the aforementioned effector mechanisms at the distal end of the flexible tube. Another way to do this is to form at least the distal end of the tube out of a sufficiently flexible material that it can be reshaped into a desired configuration. By way of example but not limitation, the distal end of the tube could be formed out of a balloon-like material that can be inflated to a desired size and shape, whereby the tissue can be manipulated as needed.

As noted above, GERD is the most common gastrointestinal problem in humans, and may be treated by altering the configuration of the esophagus and/or stomach. The present invention comprises a novel apparatus and method for manipulating the esophagus and/or stomach so as to alter the configuration of the esophagus and/or stomach and thereby treat GERD.

Furthermore, severe obesity is associated with a large number of health related problems, and may be treated by manipulating the tissues of the gastrointestinal tract to alter the size and/or shape of the stomach. The present invention provides a novel apparatus and method for manipulating the tissues of the gastrointestinal tract so as to alter the size and/or shape of the stomach and thereby treat obesity.

First Preferred Embodiment

Looking now at FIGS. 1-4, in a first preferred embodiment of the present invention, an apparatus 5 comprises a flexible tube 10 having an outer surface 15 and an inner lumen 20. Various devices (e.g., working tools, scopes, etc.) can pass through inner lumen 20. Pods 25 (shown in FIGS. 3 and 4 but omitted from the remaining drawings for purposes of clarity) are provided in the outer surface 15 of flexible tube 10, whereby tissue may be drawn to the outer surface 15 of flexible tube 10. Conduits 30 (shown in FIGS. 3 and 4 but omitted from the remaining drawings for purposes of clarity) are formed in the side wall of flexible tube 10 and supply suction to pods 25.

Effector mechanisms 35 are configured to concentrically close about flexible tube 10. Preferably, effector mechanisms 35 are pivotally mounted to flexible tube 10 by a mount 40, with actuating mechanism 45 (preferably including a flexible tube 50) being used to position flexible tube 10 and effector mechanisms 35 relative to the tissue, and to open and close effector mechanisms 35 relative to flexible tube 10. Preferably pods 25 (shown in FIGS. 3 and 4 but omitted from the remaining drawings for purposes of clarity) are also provided on the interior walls of effector mechanisms 35. Conduits 30 (shown in FIGS. 3 and 4 but omitted from the remaining drawings for purposes of clarity) may be provided in the interior walls of effector mechanisms 35 and extend out through flexible tube 50 for connection to a vacuum source.

Fixation mechanisms in the form of staples 55 (FIGS. 2 and 4) are preferably provided in the sidewall of flexible tube 10. Actuating mechanisms of the sort well known in the art (not shown) may be provided to drive staples 55 radially outward from flexible tube 10; when effector mechanisms 35 are closed down concentrically around flexible tube 10 (FIGS. 1 and 2), the effector mechanisms can serve as anvils to bend the staples closed.

Figure 5:
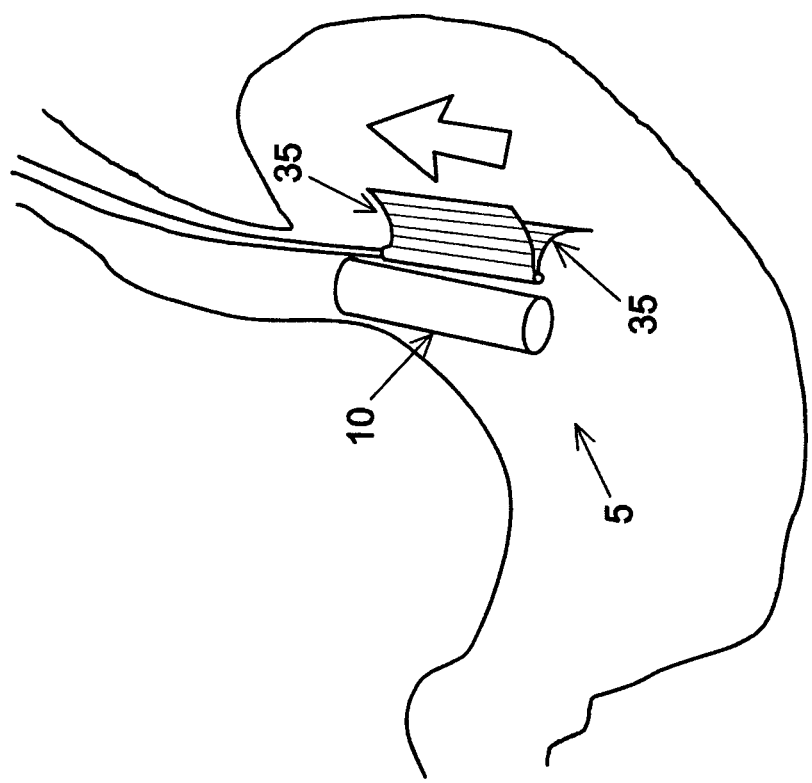
FIGS. 5-10 are a series of schematic views showing the apparatus of FIGS. 1-4 being used in a procedure to treat GERD.
Figure 6:
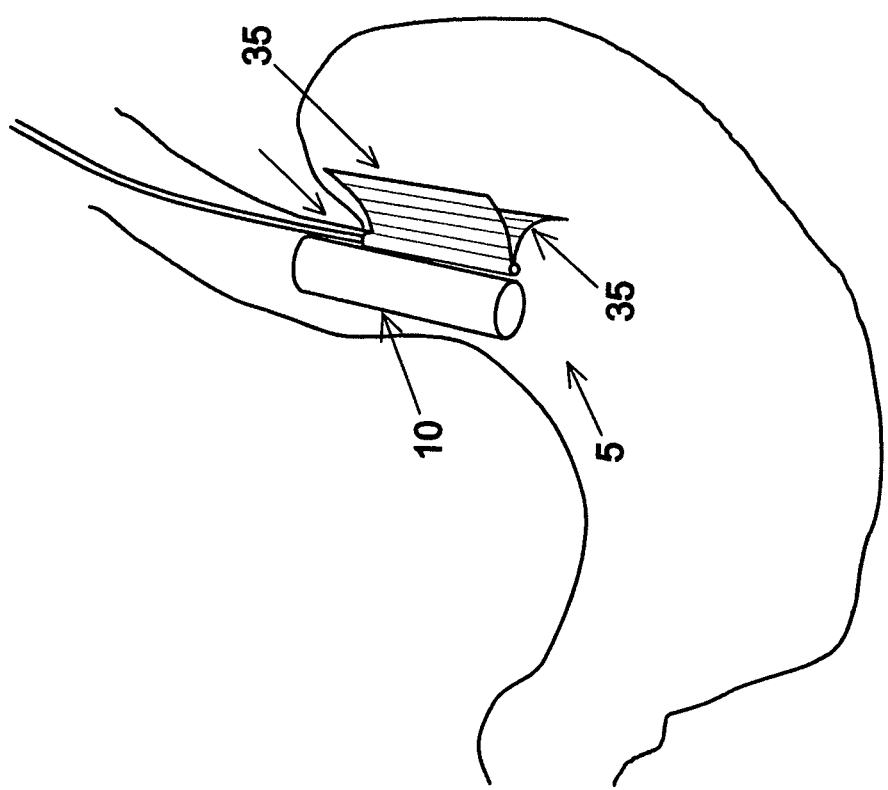
Figure 7:
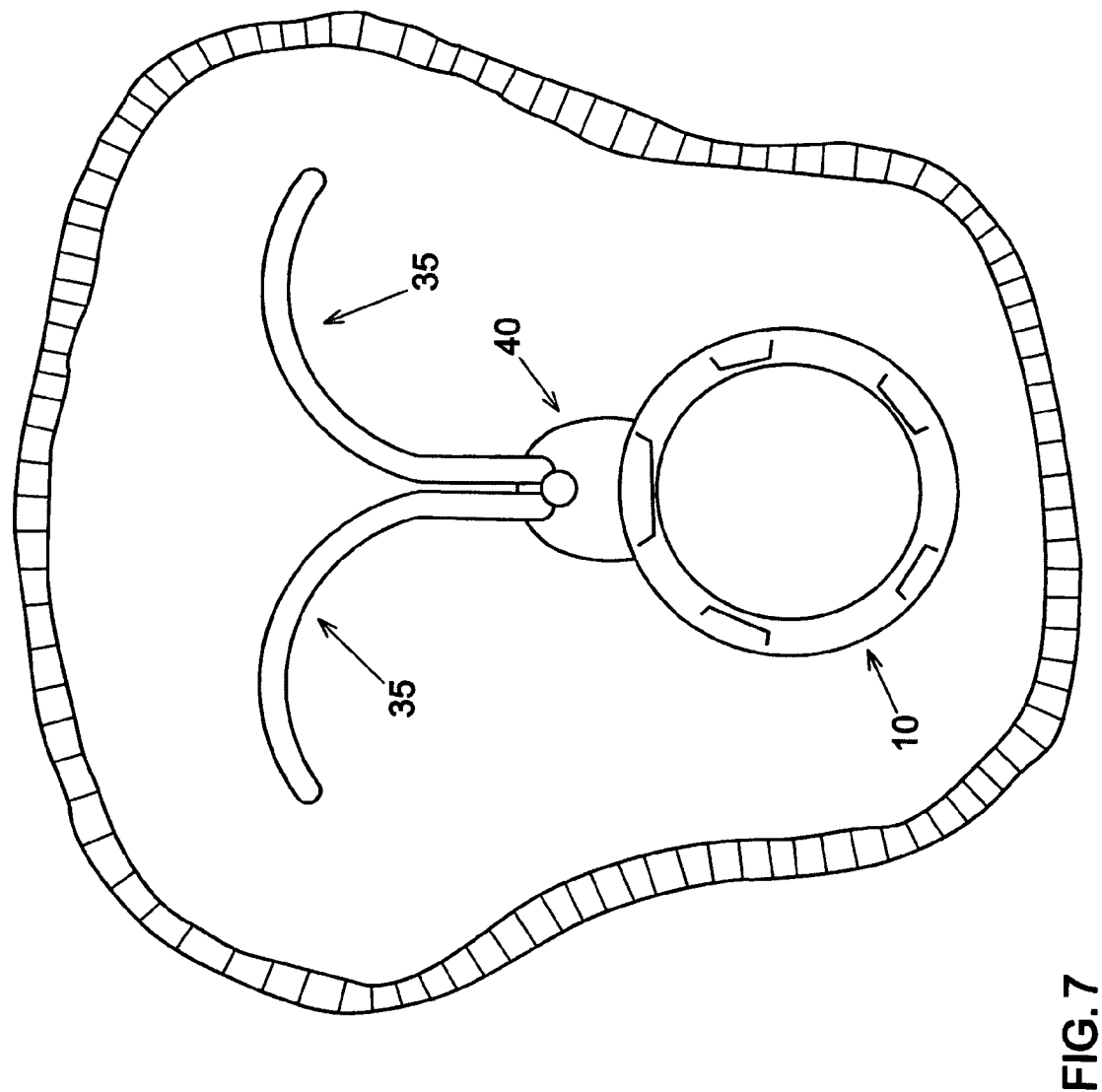
Figure 8:
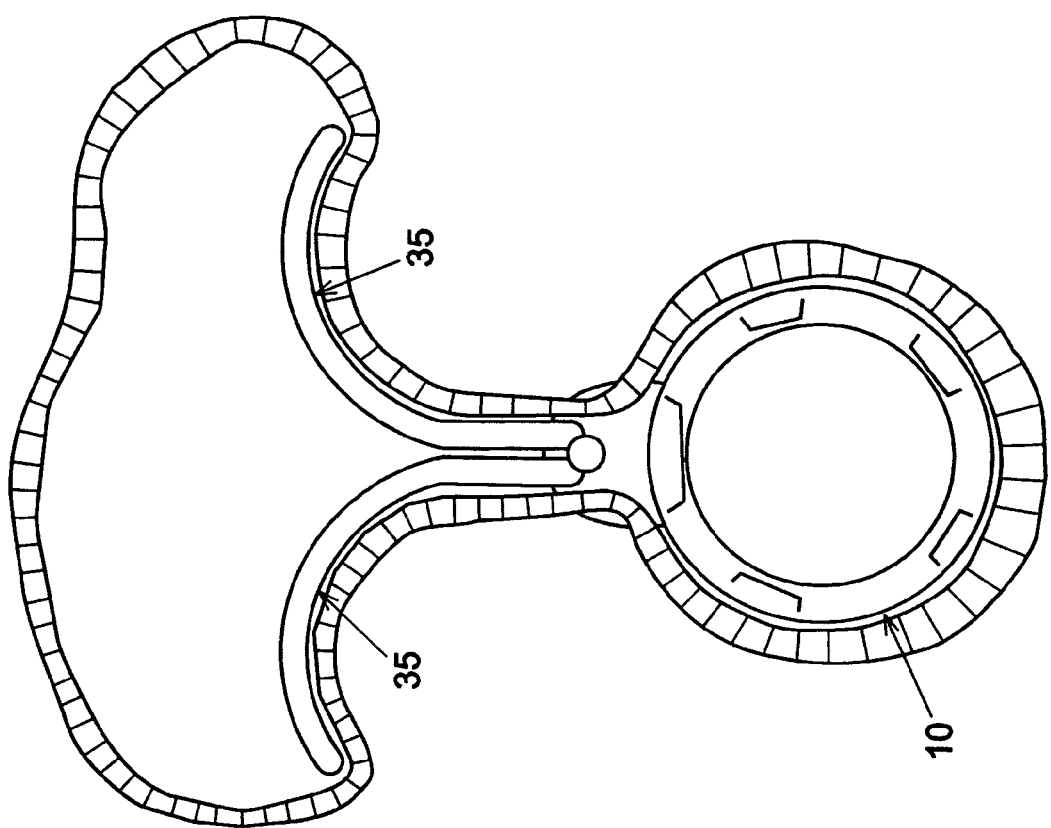
Figure 9:
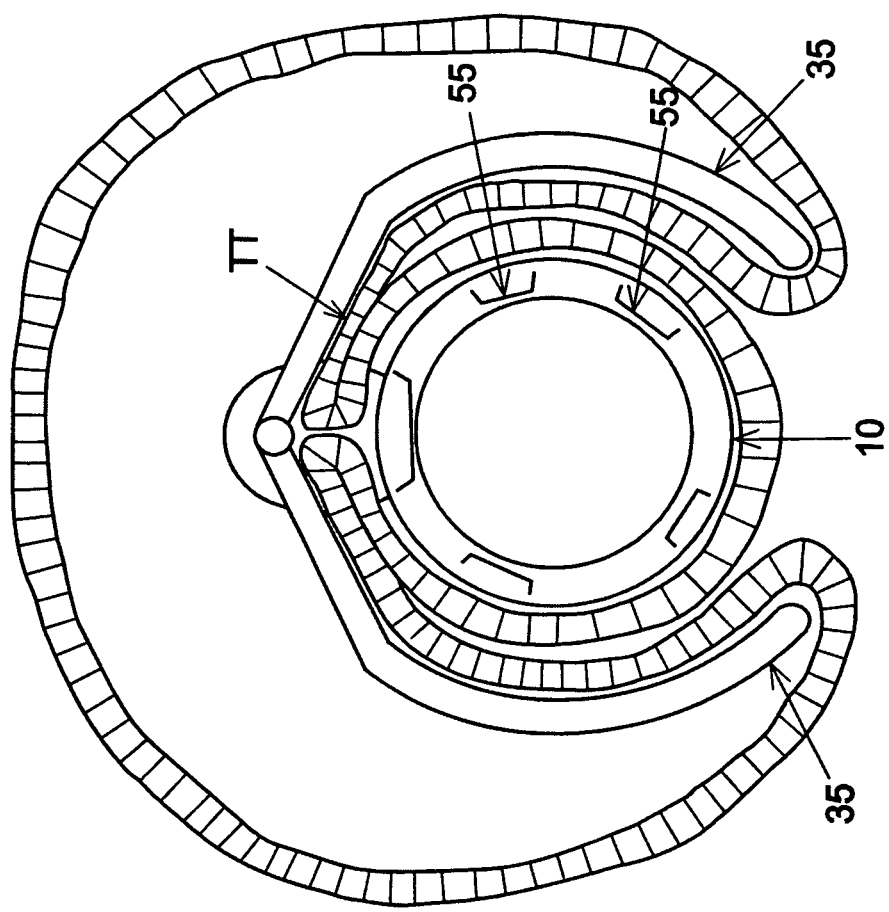
Figure 10:
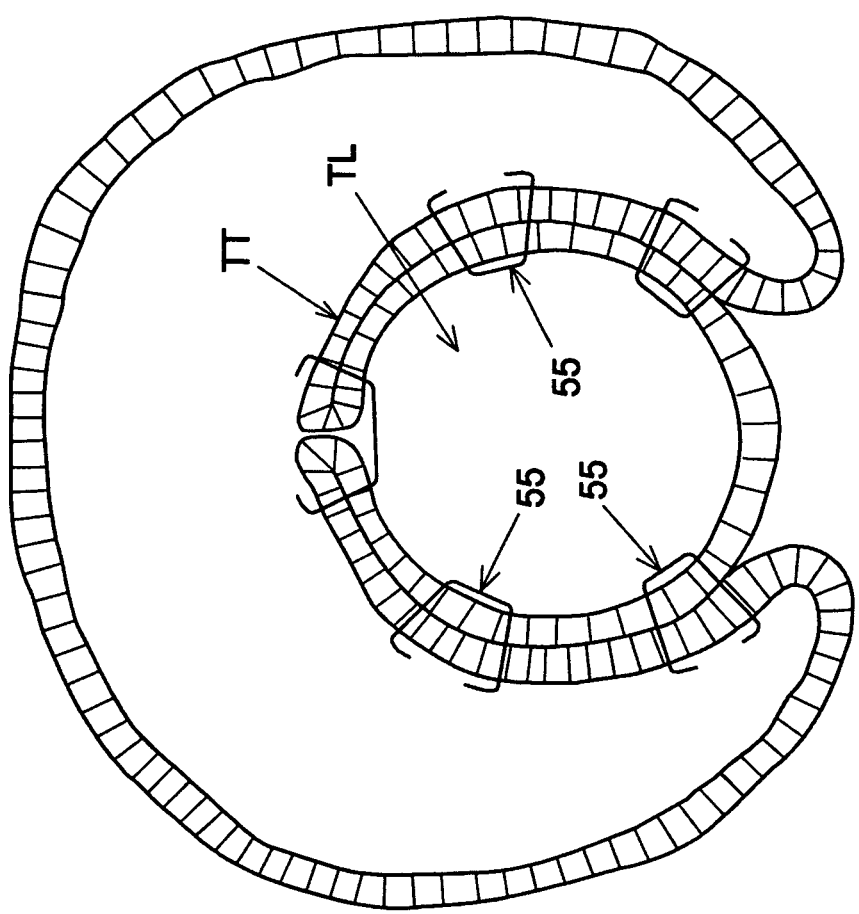

Apparatus 5 can be used to gather and fold tissue into a tube configuration, e.g., for treatment of GERD. More particularly, with effector mechanisms 35 in a closed position (e.g., FIGS. 1 and 2), apparatus 5 is advanced down the esophagus and into the stomach. Next, and looking now at FIG. 5, effector mechanisms 35 are brought to the open position in the main body of the stomach. Then apparatus 5 is brought up to the angle of the stomach near the gastroesophageal junction (FIGS. 6 and 7). Next, suction is applied to pods 25 (FIG. 8), thereby bringing tissue into proximity with outer surface of flexible tube 10 and the underside of effector wings 35. It will be appreciated that, as this occurs, the tissue brought into proximity with the outer surface of flexible tube 10 will essentially form a neoesophagus. Then, effector wings 35 are brought to the closed position (FIG. 9). In so doing, the anterior and posterior pouches of stomach are folded around the outer wall of the neoesophagus. Staples 55 may then be activated so as to hold the walls of the tube of tissue TT together and secure the wrapped pouches in place, and the apparatus 5 removed (FIG. 10). In this way, a tube of tissue TT, having a lumen TL, can be created that is surrounded by pouches of stomach that are in luminal continuity with the main lumen of the stomach. In the context of the GERD therapy, it will be appreciated that this tube is effectively a wrapped neoesophagus which may minimize gastroesophageal reflux.

Significantly, the novel apparatus and method may be used to create a tube of esophagus (e.g., neoesophagus) that may extend into the abdomen. This tube of esophagus may then be surrounded in part or completely by the stomach (i.e., the wrap). This neoesophagus may prevent reflux because the lengthening of the esophagus has caused it to be in the abdominal cavity and is thus under positive pressure. This positive pressure may cause the neoesophagus to collapse, thereby preventing reflux. This neoesophagus may also prevent reflux because it is wrapped by the stomach in such a way that the lumen of the wrap of stomach may exert a collapsible force on the esophagus and/or neoesophagus as it distends, thereby preventing reflux.

It should be appreciated that the wrap effected by apparatus 5 may be of various circumferential degree. Thus, for example, FIG. 10 depicts a wrap of approximately 270 degrees, however, this wrap could be anywhere up to 360 degrees.

Figure 11:
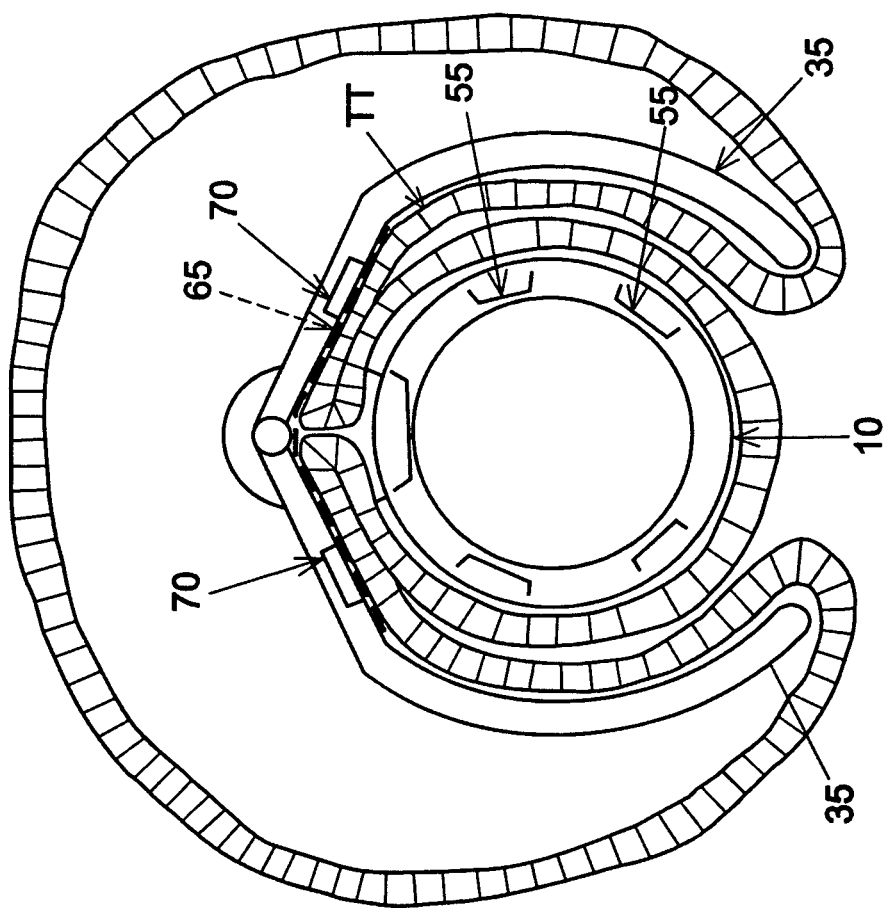
FIGS. 11 and 12 are schematic views showing an alternative form of the procedure shown in FIGS. 5-10.
Figure 12:
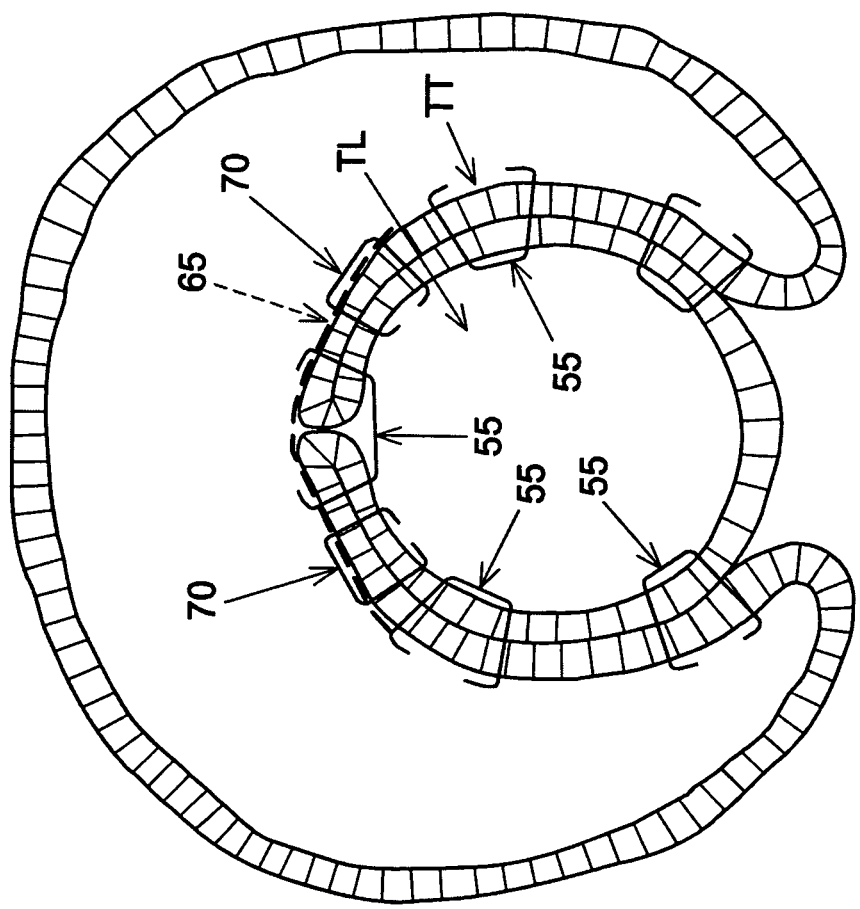
Figure 13:
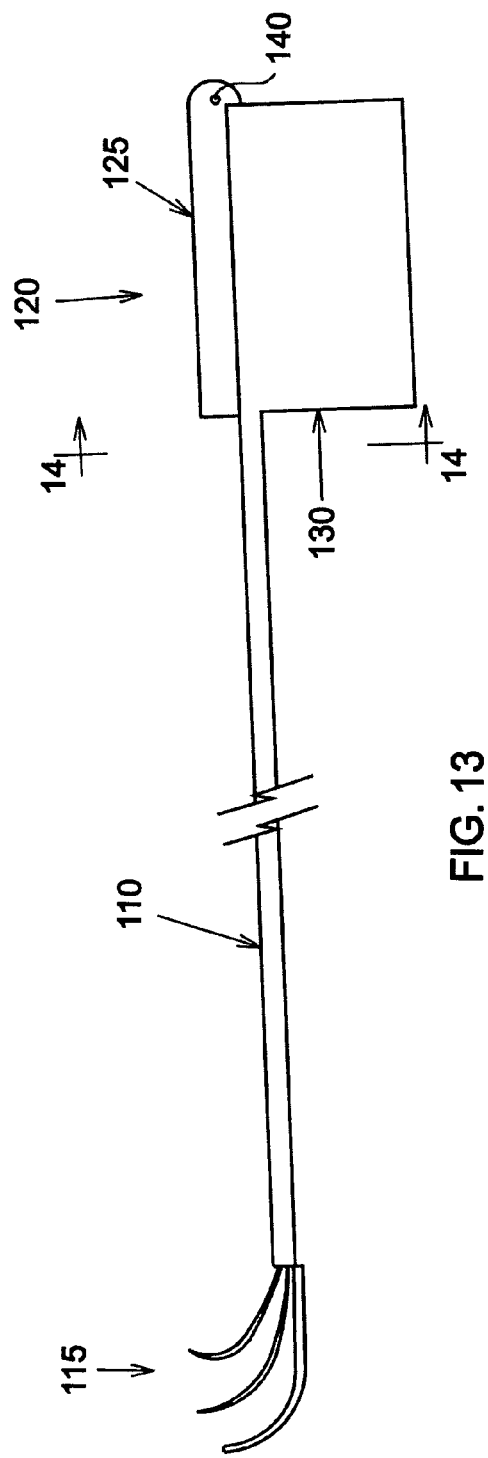
Figure 15:
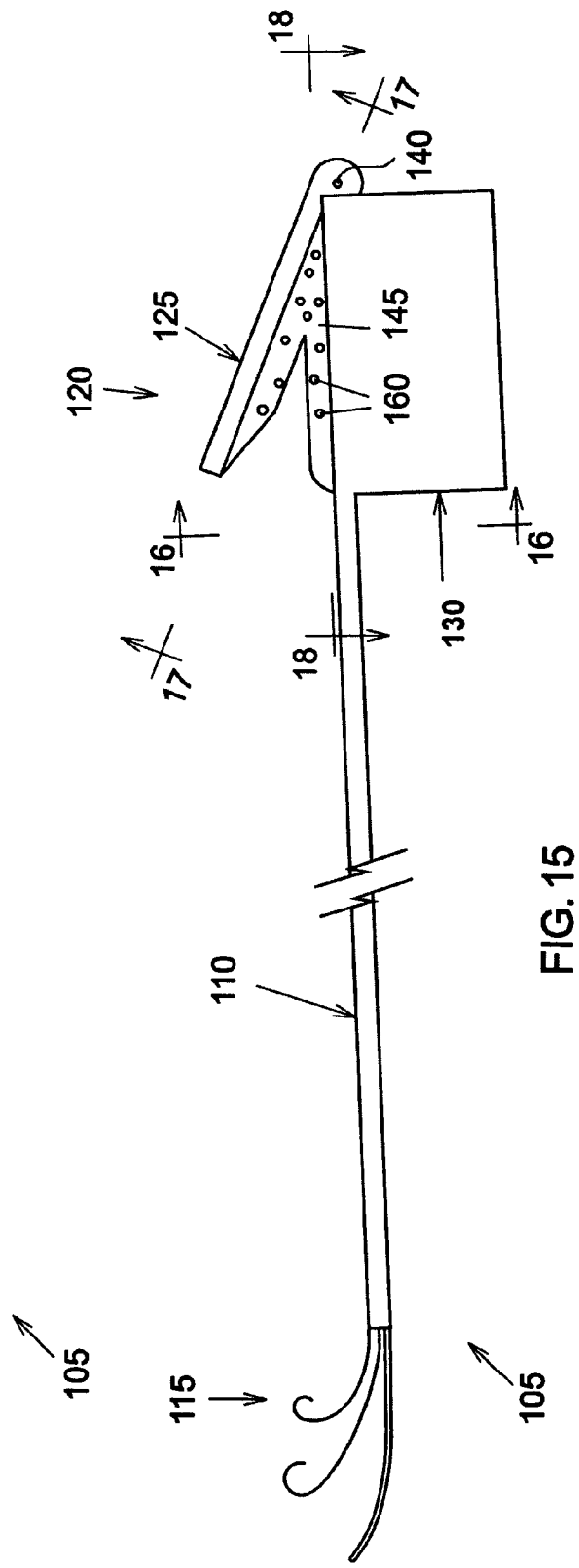
Figure 18:
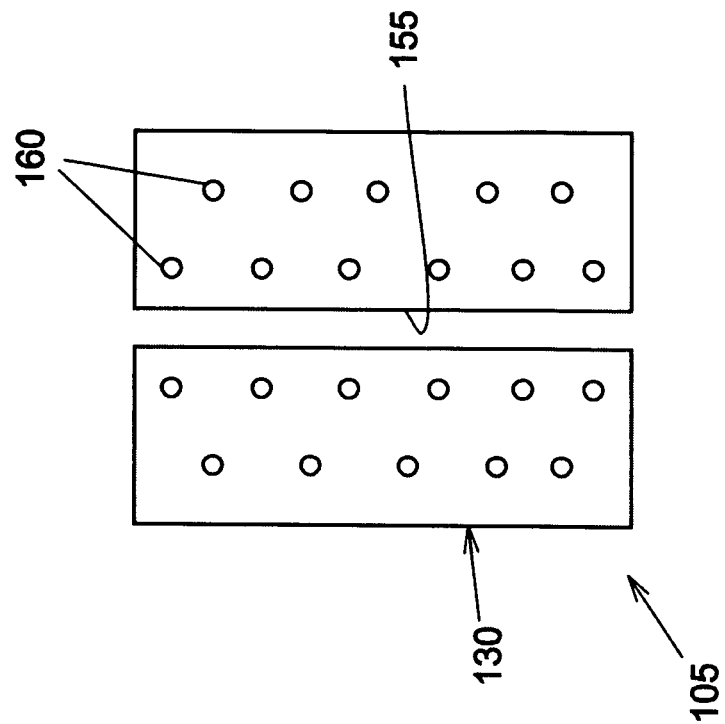
Figure 17:
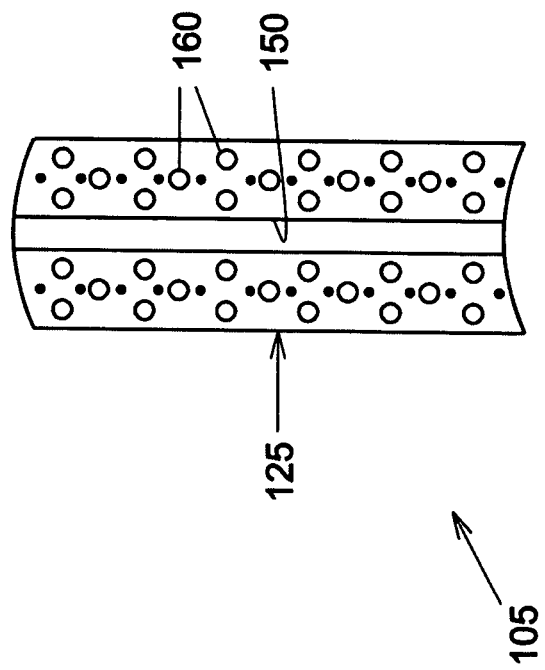

Furthermore, it should also be appreciated that, for various applications, it may be important to provide a fluidtight tube of tissue TT. Thus, for example, where the apparatus 5 is to create a wrapped neoesophagus to treat GERD, it can be important to provide a fluidtight tube of tissue TT. To this end, and looking now at FIG. 11, it may be beneficial to provide a fluidtight material 65 on the underside of effector wings 35, so that the fluidtight material 65 may be applied to outer wall of the tube of tissue TT created by apparatus 5. Staples (fired outwardly from flexible tube 10) may serve to hold the fluidtight material 65 to the outside surface of the tube of tissue TT. Alternatively, stapling mechanisms of the sort well known in the art (not shown) may be provided on the underside of effector wings 35, whereby the staples 70 (using the outside wall of flexible tube 10 as an anvil) may secure the fluidtight material 65 to the outer wall of the tube of tissue TT. See FIG. 12.

It should also be appreciated that, if desired, flexible tube 10 and effector mechanisms 35 may omit suction pods or other tissue gripping mechanisms, and the stomach tissue may be wrapped around the neoesophagus by using appropriate apparatus geometry moving about the neoesophageal fixation line. This may be facilitated by vacuum evacuation of the stomach contents to bring the stomach walls into contact with the effector arms.

Second Preferred Embodiment

Looking now at FIGS. 13-18, in a second preferred embodiment of the present invention, an apparatus 105 comprises a flexible shaft 110 with an actuator end 115 and an effector end 120. The effector end 120 has one or more effector mechanisms 125. The distal end of the device has a hollow tube 130 with a central lumen 135 (FIGS. 14 and 16). Objects such as a working instrument, endoscope, etc. can pass through the central lumen 135.

Effector mechanism 125 is adapted to open and close about an end pivot 140. A septum 145 has one portion anchored to effector mechanism 125 and another portion anchored to hollow tube 130. In one preferred construction, septum 145 enters the interior of effector mechanism 125 via a slot 150 (FIG. 16), and septum 145 enters the side wall of hollow cylinder 130 via a slot 155. The top portion of hollow tube 130, the underside of effector mechanism and/or the septum 145 have suction pods 160 disposed therein, with suction being supplied to the suction pods 160 via flexible shaft 110. In this way, effector mechanism 125 can be opened relative to hollow tube 130, suction applied to draw tissue against effector mechanism 125, hollow tube 130 and/or septum 145, and then effector mechanisms 125 closed so as to reconfigure the tissue. Preferably the underside of effector mechanism 125 includes a plurality of staples 165 which can be fired out of the bottom of effector mechanism 125 by stapling mechanisms of the sort well known in the art (not shown).

Figure 19:
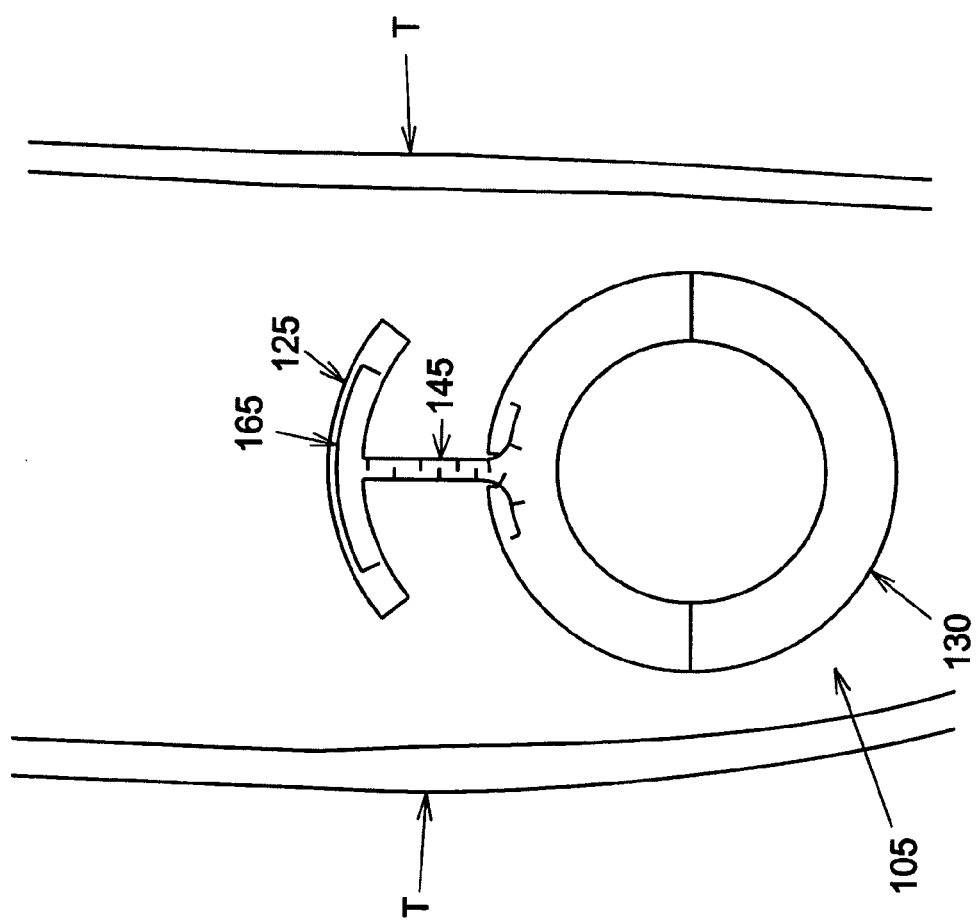
FIGS. 19-22 are a series of schematic views showing the apparatus of FIGS. 13-18 being used in a medical procedure.
Figure 20:
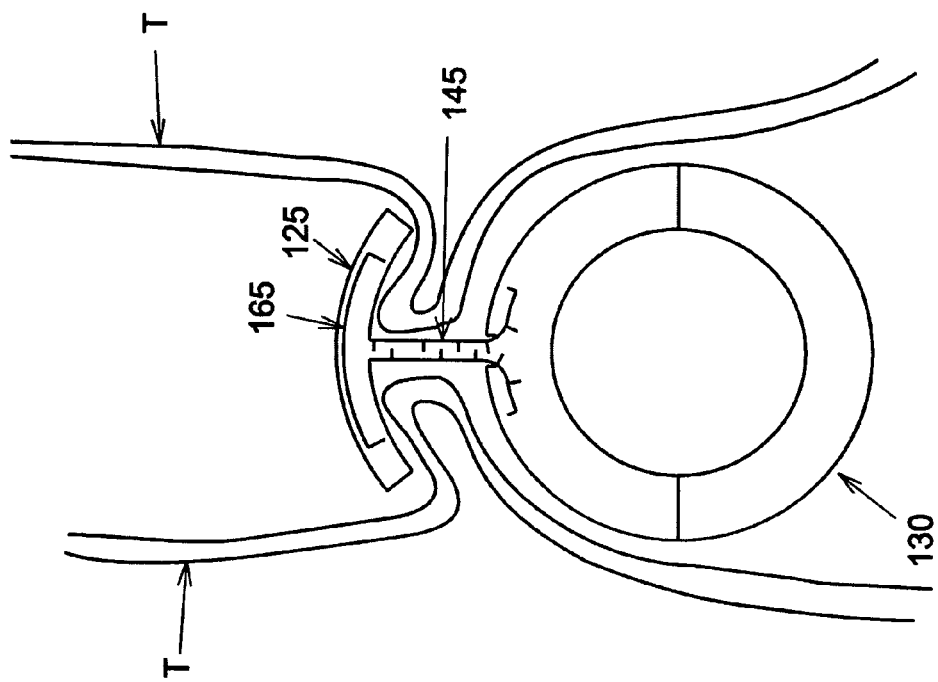
Figure 21:
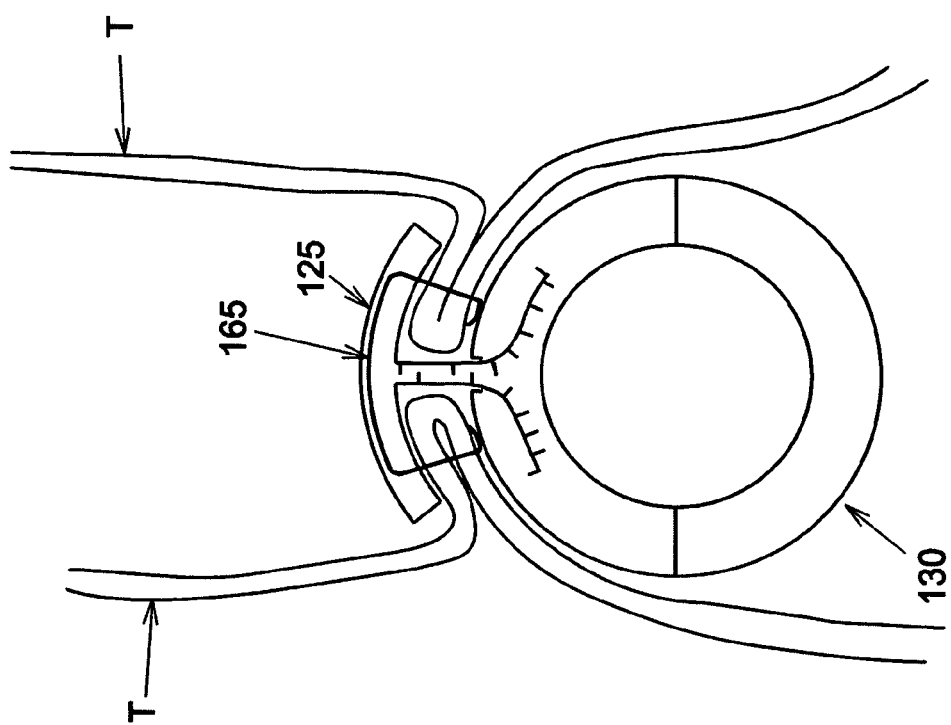
Figure 22:
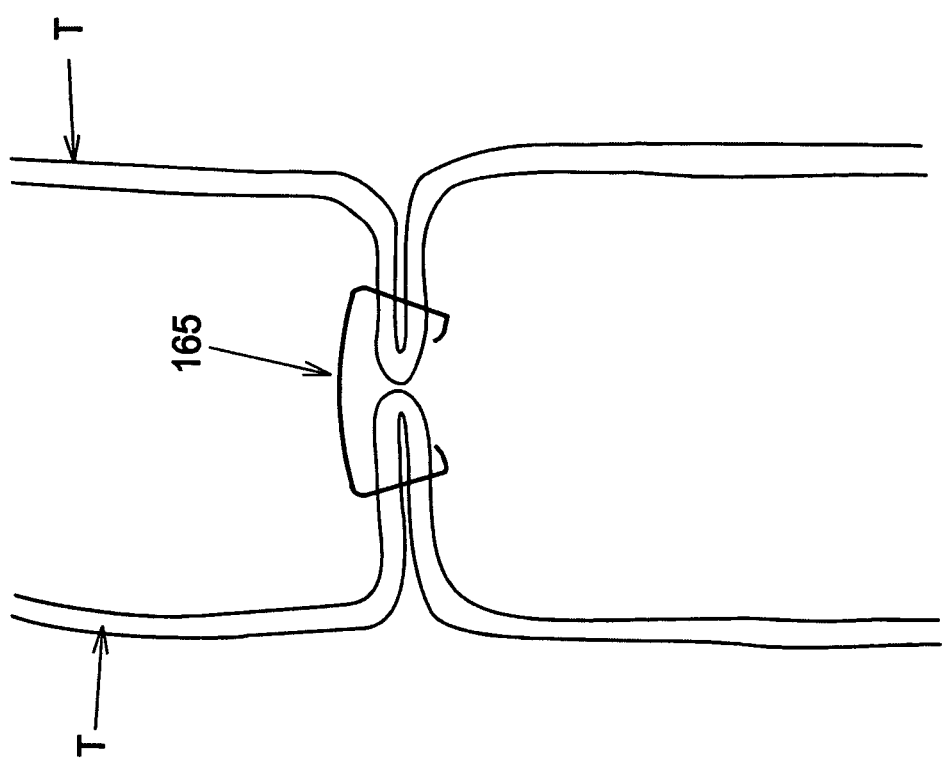

Apparatus 105 can be used in various ways to therapeutically reconfigure tissue. By way of example but not limitation, and looking now at FIGS. 19-22, apparatus 105 has its effector mechanism 125 placed into its closed position (FIGS. 13 and 14), the distal end of apparatus 105 is positioned between two opposing walls of tissue T, and effector mechanism 125 is opened (FIG. 19). Next, suction is applied so as to cause the tissue T to be drawn against effector mechanism 125, hollow tube 130 and/or septum 145 (FIG. 20). Then effector mechanism 125 is closed and staples 165 set (using the outer surface of hollow tube 130 as an anvil). See FIG. 21. Thereafter effector mechanism 125 is opened so as to release the tissue, and the apparatus withdrawn, leaving the tissue in the reconfigured arrangement shown in FIG. 22.

Figure 23:
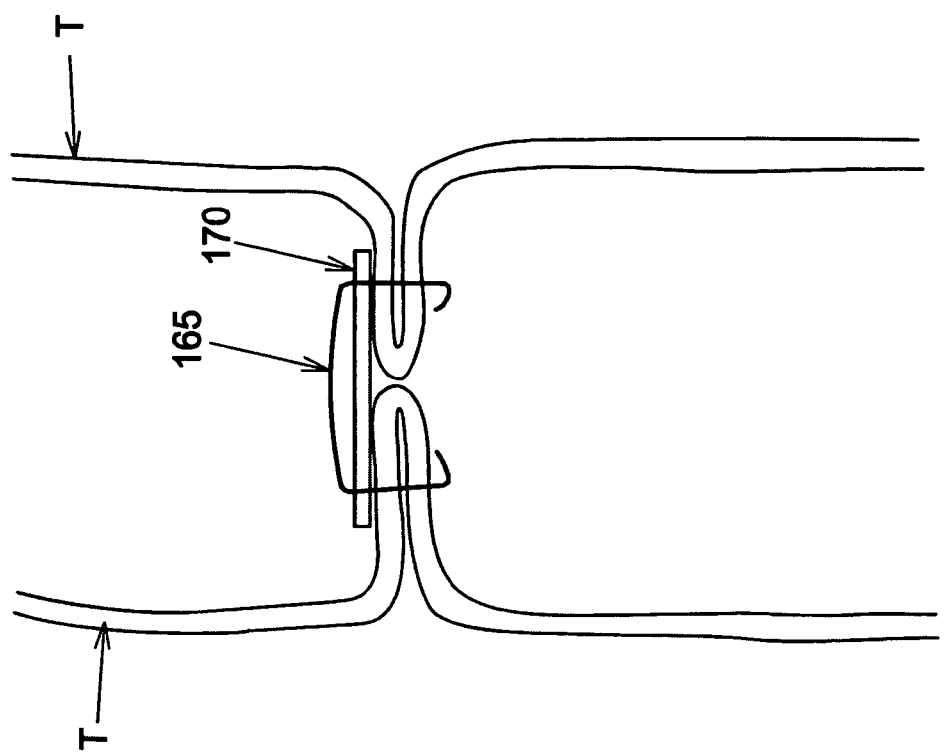

If desired, the staple 165 may be supported by one (FIG. 23) or two (FIG. 24) pieces of material 170, with the material being carried into position by effector mechanism 125 (in the example shown in FIG. 23) or by effector mechanism 125 and hollow tube 130 (in the example shown in FIG. 24).

Third Preferred Embodiment

Looking now at FIGS. 25-29, in a third preferred embodiment of the present invention, an apparatus. 205 comprises a flexible tube 210 with an outer surface 215, an inner surface 220 and a central lumen 225. The sidewall 230 of flexible tube 210 may be solid, and/or the sidewall 230 of flexible tube 210 may be hollow through which other devices such as suction tubes, cables, wires, etc. may run.

Apparatus 205 includes an effector end 235 and an actuator end 240. The effector end 235 comprises a plurality of effector mechanisms 245. The effector mechanisms 245 can be parallel to but otherwise independent of one another (e.g., as a series of independent elements collectively forming the distal end of hollow tube 210) or one or more of the effector mechanisms 245 can be connected to one another (e.g., so as to form a slotted tube configuration, such as that shown in FIGS. 25, 28 and 29). Each of the effector mechanisms 245 is provided with one or more suction pods 250 (only shown on some of the effector mechanisms 245 for clarity of illustration) for gripping tissue and one or more fastening elements 255. The fastening elements 255 may be any elements that are adapted to secure themselves to one another; in one preferred form of the invention, fastening elements 255 are magnets. The actuating end 240 has suction ports 260 which connect to suction pods 250, whereby suction may be applied to suction pods 250, and cables 270 to individually manipulate the relative position of effector mechanisms 245 (e.g., to move them longitudinally relative to the long axis of hollow tube 210, or to move them laterally relative to the longitudinal axis of hollow tube 210, etc.).

Figure 28:
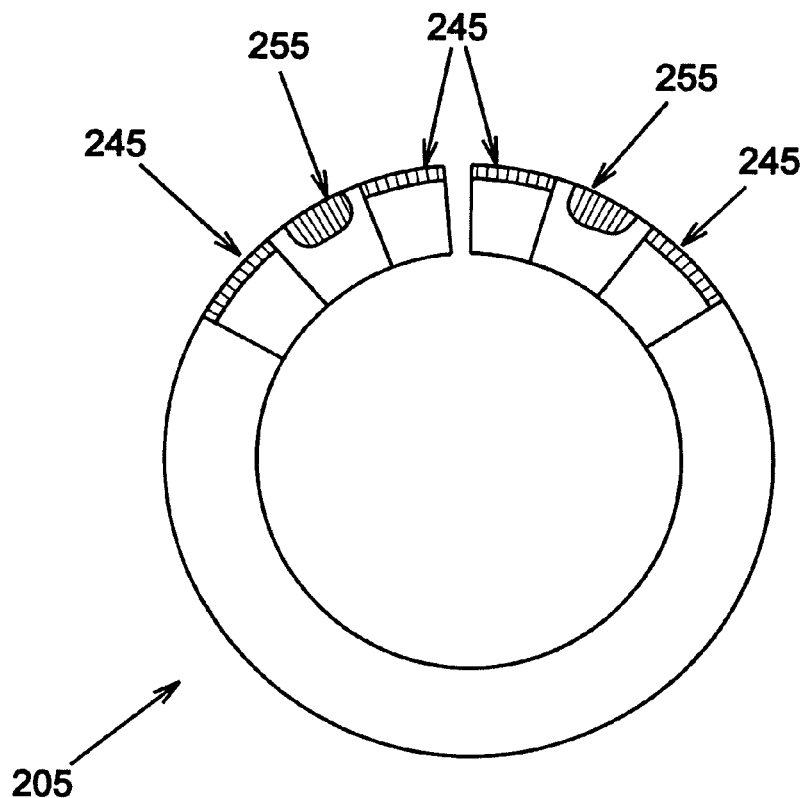
Figure 29:
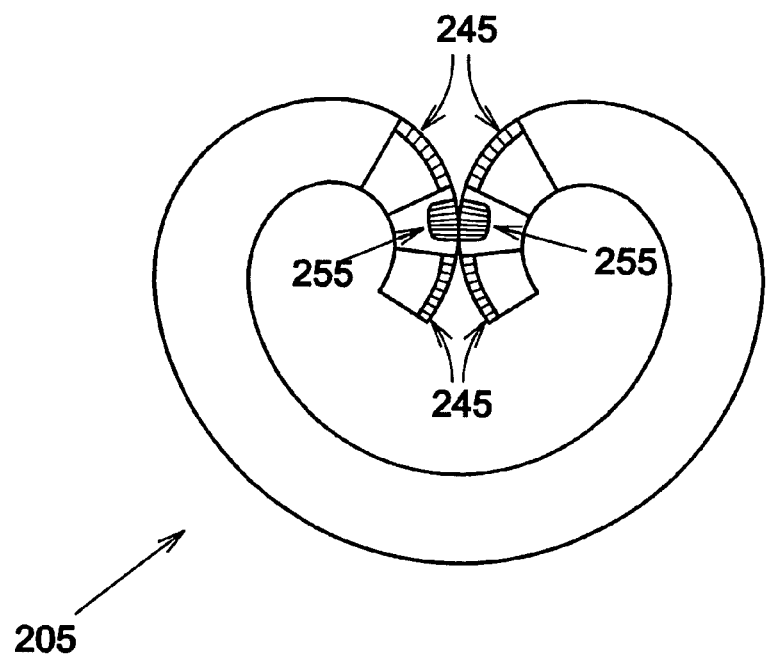

FIGS. 28 and 29 show how cables 270 may be used to manipulate the effector end 235 of hollow tube 210 from a normal round configuration (FIG. 28) to a folded configuration (FIG. 29).

As a result of the foregoing construction, it will be appreciated that tissue may first be gripped by moving the effector end 235 of tube 210 adjacent to tissue and applying suction to suction ports 260, whereby tissue will be drawn against suction pods 250, and the tissue may thereafter be folded by actuating cables 270 whereby to bring the tissue together (FIG. 29). This action simultaneously brings fastening elements 255 into proximity with each other, whereby the fastening elements 255 can secure the tissue in such position.

Figure 30:
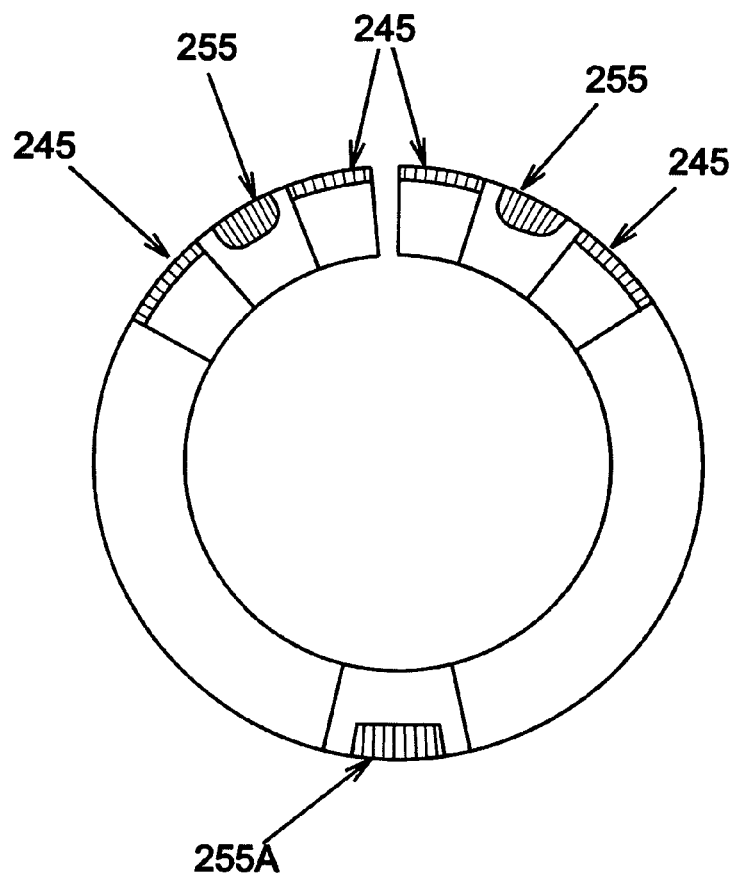
Figure 31:
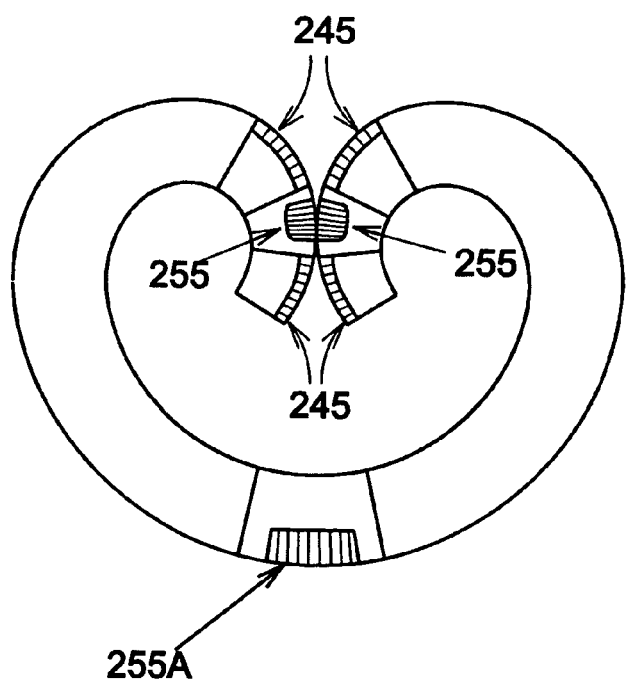

FIGS. 30 and 31 shown the same structure shown in FIGS. 29-29, except that an additional fastener element 255A is provided on the device. This additional fastening element 255A can be placed anywhere in, on or around the device so that additional folds of tissue may be created.

Additional Embodiments

It should be understood that the specific embodiments shown herein are presented by way of illustration and not limitation, and that various changes and modifications may be made by one skilled in the art without departing from the spirit and scope of the present invention.

What is claimed is:

1. Apparatus for reconfiguring tissue, said apparatus comprising:
   a shaft having a distal end and a proximal end;
   at least one effector mechanism movably mounted to said distal end of said shaft, each said effector mechanism comprising at least one gripping element for gripping tissue to that effector mechanism, said at least one effector mechanism being configured to capture the gripped tissue against said shaft;
   at least one actuating mechanism mounted to said proximal end of said shaft;
   at least one connection mechanism connecting said at least one actuating mechanism to said at least one effector mechanism, whereby a user may utilize said at least one actuating mechanism to actuate said at least one effector mechanism so as to reconfigure tissue;
   wherein said at least one effector mechanism comprises two effector mechanisms;
   wherein said two effector mechanisms are pivotally mounted to said shaft;
   wherein said distal end of said shaft comprises a longitudinal axis, and further wherein said two effector mechanisms are pivotally mounted to said shaft along a pivot axis extending parallel to said longitudinal axis of said distal end of said shaft; and
   wherein said two effector mechanisms are configured to move between (i) a closed position wherein said two effector mechanisms fold concentrically about said distal end of said shaft, and (ii) an open position wherein said two effector mechanisms rise like wings over said shaft.

2. Apparatus according to claim 1 wherein said shaft is flexible.

3. Apparatus according to claim 1 wherein said shaft has a lumen extending therethrough.

4. Apparatus according to claim 3 wherein said lumen is sized to receive another instrument therein.

5. Apparatus according to claim 4 wherein said instrument comprises a working tool.

6. Apparatus according to claim 5 wherein said working tool comprises a stapler.

7. Apparatus according to claim 4 wherein said instrument comprises a scope.

8. Apparatus according to claim 1 wherein said at least one gripping element comprises a suction pod for drawing tissue against the effector mechanism and for maintaining the tissue in such engagement while suction is maintained.

9. Apparatus according to claim 8 wherein said distal end of said shaft comprises at least one gripping element for drawing tissue against said shaft and for maintaining the tissue in such engagement while suction is maintained.

10. Apparatus according to claim 9 wherein said distal end of said shaft comprises a plurality of gripping elements, with said gripping elements being positioned about the circumference of said shaft in the region covered by said effector mechanisms when said effector mechanisms are in said closed position.

11. Apparatus according to claim 10 wherein said gripping elements comprise suction pods.

12. Apparatus according to claim 11 wherein said distal end of said shaft comprises at least one fastening mechanism for securing tissue to tissue.

13. Apparatus according to claim 12 wherein said at least one fastening mechanism is adapted to extend radially outward from said distal end of said shaft.

14. Apparatus according to claim 13 wherein said mechanism comprises a staple.

15. Apparatus according to claim 1 wherein said at least one connection mechanism comprises a cable.

16. Apparatus according to claim 1 wherein said apparatus comprises a plurality of effector mechanisms.

17. Apparatus according to claim 16 wherein said plurality of effector mechanisms extend out of the distal end of said shaft.

18. Apparatus according to claim 17 wherein said distal end of said shaft comprises a longitudinal axis, and further wherein said plurality of effector mechanisms extend parallel to said longitudinal axis of said distal end of said shaft.

19. Apparatus according to claim 18 wherein said plurality of effector mechanisms are configured to move between (i) a first position wherein said plurality of effector mechanisms collectively form a tubular configuration, and (ii) a second position wherein said plurality of effector mechanisms collectively form a non-tubular configuration.

20. Apparatus according to claim 19 wherein said plurality of gripping elements comprise at least one fastening mechanism for securing tissue.

21. Apparatus for reconfiguring tissue, said apparatus comprising:
   a shaft having a distal end and a proximal end, wherein said distal end of said shaft comprises at least one gripping element for drawing tissue against said shaft and for selectively maintaining the tissue in such engagement;
   two effector mechanisms movably mounted to said distal end of said shaft, each said effector mechanism comprising at least one gripping element for gripping tissue to that effector mechanism, said two effector mechanisms being configured to capture the gripped tissue against said shaft, wherein said distal end of said shaft comprises a longitudinal axis, wherein said two effector mechanisms are pivotally mounted to said shaft along a pivot axis extending parallel to said longitudinal axis of said distal end of said shaft, wherein said two effector mechanisms are configured to move between (i) a closed position wherein said two effector mechanisms fold concentrically about said distal end of said shaft, and (ii)

an open position wherein said two effector mechanisms rise like wings over said shaft, and wherein said at least one gripping element comprises a suction pod for drawing tissue against the effector mechanism and for maintaining the tissue in such engagement while suction is maintained;

at least one actuating mechanism mounted to said proximal end of said shaft; and at least one connection mechanism connecting said at least one actuating mechanism to said two effector mechanisms, whereby a user may utilize said at least one actuating mechanism to actuate said two effector mechanisms so as to reconfigure tissue.

22. Apparatus according to claim 21 wherein said shaft is flexible.

23. Apparatus according to claim 21 wherein said shaft has a lumen extending therethrough.

24. Apparatus according to claim 23 wherein said lumen is sized to receive another instrument therein.

25. Apparatus according to claim 24 wherein said instrument comprises a working tool.

26. Apparatus according to claim 25 wherein said working tool comprises a stapler.

27. Apparatus according to claim 24 wherein said instrument comprises a scope.

28. Apparatus according to claim 21 wherein said at least one gripping element comprises a suction pod for maintaining the tissue in such engagement while suction is maintained.

29. Apparatus according to claim 28 wherein said distal end of said shaft comprises at least one gripping element for drawing tissue against said shaft and for maintaining the tissue in such engagement while suction is maintained.

30. Apparatus according to claim 29 wherein said distal end of said shaft comprises a plurality of gripping elements, with said gripping elements being positioned about the circumference of said shaft in the region covered by said effector mechanisms when said effector mechanisms are in said closed position.

31. Apparatus according to claim 30 wherein said gripping elements comprise suction pods.

32. Apparatus according to claim 31 wherein said distal end of said shaft comprises at least one fastening mechanism for securing tissue to tissue.

33. Apparatus according to claim 32 wherein said at least one fastening mechanism is adapted to extend radially outward from said distal end of said shaft.

34. Apparatus according to claim 33 wherein said fastening mechanism comprises a staple.

* * * * *